US010266851B2

(12) United States Patent
Chen

(10) Patent No.: US 10,266,851 B2
(45) Date of Patent: Apr. 23, 2019

(54) USING PROGRAMMABLE DNA BINDING PROTEINS TO ENHANCE TARGETED GENOME MODIFICATION

(71) Applicant: SIGMA-ALDRICH CO., LLC, St. Louis, MO (US)

(72) Inventor: Fuqiang Chen, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 0 days.

(21) Appl. No.: 15/437,148

(22) Filed: Feb. 20, 2017

(65) Prior Publication Data

US 2017/0349913 A1    Dec. 7, 2017

Related U.S. Application Data

(60) Provisional application No. 62/344,858, filed on Jun. 2, 2016, provisional application No. 62/358,415, filed on Jul. 5, 2016.

(51) Int. Cl.
   *C12N 9/22* (2006.01)
   *C12N 15/10* (2006.01)
   *C12N 15/90* (2006.01)

(52) U.S. Cl.
   CPC ............. *C12N 15/907* (2013.01); *C12N 9/22* (2013.01); *C12N 15/102* (2013.01)

(58) Field of Classification Search
   None
   See application file for complete search history.

(56) References Cited

U.S. PATENT DOCUMENTS

| | | | |
|---|---|---|---|
| 8,546,553 B2 | 10/2013 | Terns et al. | |
| 8,697,359 B1 | 4/2014 | Zhang | |
| 8,993,233 B2 | 3/2015 | Zhang et al. | |
| 9,023,649 B2 | 5/2015 | Mali et al. | |
| 9,260,723 B2 | 2/2016 | Mali et al. | |
| 9,745,562 B2 * | 8/2017 | Donohoue | C12N 15/907 |
| 9,970,030 B2 * | 5/2018 | Cameron | C12N 15/111 |
| 2005/0220796 A1 | 10/2005 | Dynan et al. | |
| 2007/0134796 A1 | 6/2007 | Holmes et al. | |
| 2007/0218528 A1 | 9/2007 | Miller | |
| 2010/0055728 A1 | 3/2010 | Yang et al. | |
| 2010/0076057 A1 | 3/2010 | Sontheimer et al. | |
| 2011/0189776 A1 | 8/2011 | Terns et al. | |
| 2011/0201773 A1 | 8/2011 | Bonzi et al. | |
| 2011/0207221 A1 | 8/2011 | Cost et al. | |
| 2011/0217739 A1 | 9/2011 | Terns et al. | |
| 2011/0223638 A1 | 9/2011 | Wiedenheft et al. | |
| 2012/0164125 A1 | 6/2012 | Sera | |
| 2012/0192298 A1 | 7/2012 | Weinstein et al. | |
| 2013/0130248 A1 | 5/2013 | Haurwitz et al. | |
| 2013/0196373 A1 | 8/2013 | Gregory et al. | |
| 2013/0326645 A1 | 12/2013 | Cost et al. | |
| 2014/0068797 A1 | 3/2014 | Doudna et al. | |
| 2014/0273230 A1 | 9/2014 | Chen et al. | |
| 2014/0273233 A1 | 9/2014 | Chen et al. | |
| 2014/0315985 A1 | 10/2014 | May et al. | |
| 2015/0044772 A1 | 2/2015 | Zhao | |
| 2016/0002670 A1 | 1/2016 | Church et al. | |
| 2016/0017366 A1 | 1/2016 | Chen et al. | |
| 2016/0177278 A1 * | 6/2016 | Wolfe | C12N 9/22 435/199 |
| 2016/0208243 A1 * | 7/2016 | Zhang | C12N 15/8201 |
| 2016/0298125 A1 | 10/2016 | Chen et al. | |
| 2017/0058298 A1 * | 3/2017 | Kennedy | C12N 9/22 |
| 2017/0314002 A1 * | 11/2017 | Gong | C12N 15/62 |

FOREIGN PATENT DOCUMENTS

| | | |
|---|---|---|
| CN | 103233028 A | 8/2013 |
| CN | 103343120 A | 10/2013 |
| CN | 103388006 A | 11/2013 |
| GB | 1506509.7 * | 5/2015 |
| WO | 00/41566 A1 | 7/2000 |
| WO | 01/02019 A2 | 1/2001 |
| WO | 01/83751 A2 | 11/2001 |
| WO | 03/046141 A2 | 6/2003 |
| WO | 2005/014791 A2 | 2/2005 |
| WO | 2008/108989 A2 | 9/2008 |
| WO | 2010/054108 A2 | 5/2010 |
| WO | 2010/075424 A2 | 7/2010 |
| WO | 2011/146121 A1 | 11/2011 |
| WO | 2012/012738 A1 | 1/2012 |
| WO | 2012/164565 A1 | 12/2012 |
| WO | 2013/098244 A1 | 7/2013 |
| WO | 2013/141680 A1 | 9/2013 |
| WO | 2013/142578 A1 | 9/2013 |
| WO | 2013/176772 A1 | 11/2013 |
| WO | 2014/065596 A1 | 5/2014 |
| WO | 2014/089290 A1 | 6/2014 |

(Continued)

OTHER PUBLICATIONS

Sinkunas et al. Cas3 nuclease-helicase activity assays. Methods in Molecular Biology, vol. 1311, pp. 277-291, 2015.*
Zhang et al. Multiple nucleic acid cleavage modes in divergent type III CRISPR systems. Nucleic Acids Research, vol. 44, No. 4, pp. 1789-1799, Jan. 21, 2016.*
Fernandes et al. Type II and type V CRISPR effector nucleases from a structural biologists perspective. Postepy Biochemii, vol. 62, No. 3, pp. 315-326, Jul. 2016.*
Barkal et al. Cas9 functionally opens chromatin. PLOS ONE, vol. 11, No. 3, e0152683, Mar. 31, 2016, printed as pp. 1/8-8/8. (Year: 2016).*
Burstein et al., "New CRISPR-Cas systems from uncultivated microbes", Nature, 2017, pp. 237-241, vol. 542.

(Continued)

*Primary Examiner* — Jennifer Dunston
(74) *Attorney, Agent, or Firm* — Benjamin J. Sodey

(57) ABSTRACT

Compositions and methods for using programmable DNA binding proteins to increase the efficiency and/or specificity of targeted genome modification or to facilitate the detection of specific genomic loci in eukaryotic cells.

18 Claims, 10 Drawing Sheets
(10 of 10 Drawing Sheet(s) Filed in Color)
Specification includes a Sequence Listing.

(56) References Cited

FOREIGN PATENT DOCUMENTS

| WO | 2014/093655 A2 | 6/2014 | | |
|---|---|---|---|---|
| WO | 2014/099744 A1 | 6/2014 | | |
| WO | 2014/099750 A2 | 6/2014 | | |
| WO | 2014/144288 A1 | 9/2014 | | |
| WO | 2014/150624 A1 | 9/2014 | | |
| WO | 2014/191518 A1 | 12/2014 | | |
| WO | 2014/197568 A2 | 12/2014 | | |
| WO | 2014/197748 A2 | 12/2014 | | |
| WO | 2015/127439 A1 | 8/2015 | | |
| WO | 2016/007604 A1 | 1/2016 | | |
| WO | 2016/022363 A2 | 2/2016 | | |
| WO | 2016/028682 A1 | 2/2016 | | |
| WO | 2016/036754 A1 | 3/2016 | | |
| WO | WO-2016065364 A1 | * | 4/2016 | C12N 9/22 |
| WO | 2016/073990 A2 | 5/2016 | | |
| WO | WO 2016166340 A1 | * | 10/2016 | C12N 9/22 |
| WO | 2017/070598 A1 | 4/2017 | | |
| WO | 2017/096328 A1 | 6/2017 | | |

OTHER PUBLICATIONS

Chen et al., "Dynamic Imaging of Genomic Loci in Living Human Cells by an Optimized CRISPR/Cas System", Cell, 2013, pp. 1479-1491, vol. 155.
Chereji et al., "Functional roles of nucleosome stability and dynamics", Briefings in Functional Genomics, 2014, pp. 50-60, vol. 14, No. 1.
Chung et al., "Human Embryonic Stem Cell Lines Generated without Embryo Destruction", Cell Stem Cell, 2008, pp. 113-117, vol. 2.
Cong et al., "Multiplex Genome Engineering Using CRISPR/Cas Systems", Science, 2013, pp. 819-823, vol. 339.
Cradick et al., "CRISPR/Cas9 systems targeting β-globin and CCR5 genes have substantial off-target activity", Nucleic Acids Research, 2013, pp. 9584-9592, vol. 41, No. 20.
Deng et al., "CASFISH: CRISPR/Cas9-mediated in situ labeling of genomic loci in fixed cells", PNAS, 2015, pp. 11870-11875, vol. 112, No. 38.
Fu et al., "High-frequency off-target mutagenesis induced by CRISPR-Cas nucleases in human cells", Nature Biotechnology, 2013, pp. 822-826, vol. 31.
Gaj et al., "ZFN, TALEN and CRISPR/Cas-based methods for genome engineering", Trends Biotechnol., 2013, pp. 397-405, vol. 31, No. 7.
Gilbert et al., "Genome-Scale CRISPR-Mediated Control of Gene Repression and Activation", Cell, 2014, pp. 647-661, vol. 159, No. 3.
Gribskov et al., "Sigma factors from E. coli, B. subtilis, phage SP01, and phage T4 are homologous proteins", Nucleic Acids Research, 1986, pp. 6745-6763, vol. 14, No. 16.
Hilton et al., "Epigenome editing by a CRISPR/Cas9-based acetyltransferase activates genes from promoters and enhancers", Nat Biotechnol., 2015, pp. 510-517, vol. 33, No. 5.
Jinek et al., "A Programmable Dual-RNA-Guided DNA Endonuclease in Adaptive Bacterial Immunity", Science, 2012, pp. 816-821, vol. 337.
Komor et al., "Programmable editing of a target base in genomic DNA without double-stranded DNA cleavage", Nature, 2016, pp. 420-424, vol. 533.
Konermann et al., "Genome-scale transcriptional activation by an engineered CRISPR-Cas9 complex", Nature, 2015, pp. 583-588, vol. 517.
Koos et al., "Proximity-dependent initiation of hybridization chain reaction", Nature Communications, 2015, pp. 1-10, vol. 6, 7294.
Lin et al., "CRISPR/Cas9 systems have off-target activity with insertions or deletions between target DNA and guide RNA sequences", Nucleic Acids Research, 2014, pp. 7473-7485, vol. 42, No. 11.
Lombardo et al., "Gene editing in human stem cells using zinc finger nucleases and integrase-defective lentiviral vector delivery", Nature Biotechnology, 2007, pp. 1298-1306, vol. 25, No. 11.
Mali et al., "RNA-Guided Human Genome Engineering via Cas9", Science, 2013, pp. 823-826, vol. 339.
Moehle et al., "Targeted gene addition into a specified location in the human genome using designed zinc finger nucleases", PNAS, 2007, pp. 3055-3060, vol. 104, No. 9.
Sanjana et al., "A Transcription Activator-Like Effector (TALE) Toolbox for Genome Engineering", Nat Protoc., 2012, pp. 171-192, vol. 7, No. 1.
Santiago et al., "Targeted gene knockout in mammalian cells by using engineered zinc-finger nucleases", PNAS, 2008, pp. 5809-5814, vol. 105, No. 15.
Smith et al., "Comparison of Biosequences", Advances in Applied Mathematics, 1981, pp. 482-489, vol. 2.
Soderberg et al., "Direct observation of individual endogenous protein complexes in situ by proximity ligation", Nature Methods, 2006, pp. 995-1000, vol. 3, No. 12.
Urnov et al., "Highly efficient endogenous human gene correction using designed zinc-finger nucleases", Nature, 2005, pp. 646-651, vol. 435.
Wu et al., "Genome-wide binding of the CRISPR endonuclease Cas9 in mammalian cells", Nat Biotechnol., 2014, pp. 670-676, vol. 32, No. 7.
Zalatan et al., "Engineering Complex Synthetic Transcriptional Programs with CRISPR RNA Scaffolds", Cell, 2015, pp. 339-350, vol. 160.
Zetsche et al., "Cpf1 is a single RNA-guided endonuclease of a Class 2 CRISPR-Cas system", Cell, 2015, pp. 759-771, vol. 163, No. 3.
Al-Attar et al., "Clustered regularly interspaced short palindromic repeats (CRISPRs): the hallmark of an ingenious antiviral defense mechanism in prokaryotes", Biological Chemistry, 2011, pp. 277-289, vol. 392, No. 4.
Alberts et al., "Molecular Biology of The Cell", 2002, 4th Ed., Garland Science, New York, NY, p. 244.
Barrangou, "RNA-mediated programmable DNA cleavage", Nature Biotechnology, 2012, pp. 836-838, vol. 30, No. 9.
Barrangou, "CRISPR-Cas systems and RNA-guided interference", Wiley Interdisciplinary Reviews: RNA, 2013, pp. 267-278, vol. 4, No. 3.
Bassett et al., "Highly Efficient Targeted Mutagenesis of Drosophila with the CRISPR/Cas9 System", Cell Reports, 2013, pp. 220-228, vol. 4.
Beerli et al., "Engineering polydactyl zinc-finger transcription factors", Nature Biotechnology, 2002, pp. 135-141, vol. 20.
Belfort et al., "Homing endonucleases: keeping the house in order", Nucleic Acids Research, 1997, pp. 3379-3388, vol. 25, No. 17.
Bikard et al., "Programmable repression and activation of bacterial gene expression using an engineered CRISPR-Cas system", Nucleic Acids Research, 2013, pp. 7429-7437, vol. 41, No. 15.
Bitinaite et al., "FokI dimerization is required for DNA cleavage", PNAS, 1998, pp. 10570-10575, vol. 95.
Bogdanove et al., "TAL Effectors: Customizable Proteins for DNA Targeting", Science, 2011, pp. 1843-1846, vol. 333, No. 6051.
Carroll, "A CRISPR Approach to Gene Targeting", Molecular Therapy, 2012, pp. 1658-1660, vol. 20, No. 9.
Chalaya et al., "Tissue Specificity of Methylation of Cytosines in Regulatory Regions of Four Genes Located in the Locus FXYD5-COX7A1 of Human Chromosome 19: Correlation with Their Expression Level", Biochemistry (Moscow), 2006, pp. 294-299, vol. 71, No. 3.
Charpentier et al., "Biotechnology: Rewriting a genome", Nature, 2013, pp. 50-51, vol. 495, No. 7439.
Chen et al., "Transfection and expression of plasmid DNA in plant cells by an arginine-rich intracellular delivery peptide without protoplast preparation", FEBS Letters, 2007, pp. 1891-1897, vol. 581.
Cho et al., "Targeted genome engineering in human cells with the Cas9 RNA-guided endonuclease", Nature Biotechnology, 2013, pp. 230-232, vol. 31, No. 3.

(56) References Cited

OTHER PUBLICATIONS

Choo et al., "Advances in zinc finger engineering", Current Opinion in Structural Biology, 2000, pp. 411-416, vol. 10.
Christian et al., "Targeting DNA Double-Strand Breaks with TAL Effector Nucleases", Genetics, 2010, pp. 757-761, vol. 186, No. 2, including 8 pgs. of Supporting Information.
Cristea et al., "In vivo Cleavage of Transgene Donors Promotes Nuclease-Mediated Targeted Integration", Biotechnology and Bioengineering, 2012, pp. 871-880, vol. 110, No. 3.
Deltcheva et al., "CRISPR RNA maturation by trans-encoded small RNA and host factor RNase III", Nature, 2011, pp. 602-607, vol. 471.
Deng et al., "Structural Basis for Sequence-Specific Recognition of DNA by TAL Effectors", Science, 2012, pp. 720-723, vol. 335.
Doyon et al., "Heritable Targeted Gene Disruption in Zebrafish Using Designed Zinc Finger Nucleases", Nature Biotechnology, 2008, pp. 702-708, vol. 26, No. 6.
Doyon et al., "Enhancing zinc-finger-nuclease activity with improved obligate heterodimeric architectures", Nature Methods, 2011, pp. 74-79, vol. 8, No. 1.
Durai et al., "Zinc finger nucleases: custom-designed molecular scissors for genome engineering of plant and mammalian cells", Nucleic Acids Research, 2005, pp. 5978-5990, vol. 33, No. 18.
Farzadfard et al., "Tunable and Multifunctional Eukaryotic Transcription Factors Based on CRISPR/Cas", ACS Synthetic Biology, 2013, pp. 604-613, vol. 2, No. 10.
Fonfara et al., "Creating highly specific nucleases by fusion of active restriction endonucleases and catalytically inactive homing endonucleases", Nucleic Acids Research, 2011, pp. 1-14.
Friedland et al., "Heritable genome editing in C. elegans via a CRISPR-Cas9 system", Nature Methods, 2013, pp. 741-743, vol. 10, No. 8.
Gasiunas et al., "Cas9-crRNA ribonucleoprotein complex mediates specific DNA cleavage for adaptive immunity in bacteria", PNAS, 2012, pp. E2579-E2586, vol. 109, No. 39.
Gilbert et al., "CRISPR-Mediated Modular RNA-Guided Regulation of Transcription in Eukaryotes", Cell, 2013, pp. 442-451, vol. 154, No. 2, including 5 pgs. of Supplemental Information.
Gunther, "Concentration, compartmentation and metabolic function of intracellular free Mg2+", Magnesium Research, 2006, pp. 225-236, vol. 19, No. 4.
Gustafsson et al., "Codon bias and heterologous protein expression", Trends in Biotechnology, 2004, pp. 346-353, vol. 22, No. 7.
Haft et al., "A Guild of 45 CRISPR-Associated (Cas) Protein Families and Multiple CRISPR/Cas Subtypes Exist in Prokaryotic Genomes", PLoS Computational Biology, 2005, e60, pp. 0474-0483, vol. 1, No. 6.
Hale et al., "Essential Features and Rational Design of CRISPR RNAs that Function with the Gas RAMP Module Complex to Cleave RNAs", Molecular Cell, 2012, pp. 292-302, vol. 45, No. 3.
Han et al., "Efficient Intracellular Delivery of GFP by Homeodomains of *Drosophila* Fushi-tarazu and Engrailed Proteins", Molecules and Cells, 2000, pp. 728-732, vol. 10, No. 6.
Hsu et al., "DNA targeting specificity of RNA-guided Cas9 nucleases", Nature Biotechnology, 2013, pp. 827-832, vol. 31, No. 9.
Hwang et al., "Efficient genome editing in zebrafish using a CRISPR-Cas system", Nature Biotechnology, 2013, pp. 227-229, vol. 31, No. 3.
Isalan et al., "A rapid, generally applicable method to engineer zinc fingers illustrated by targeting the HIV-1 promoter", Nature Biotechnology, 2001, pp. 656-660, vol. 19, No. 7.
Iseli et al., "Indexing Strategies for Rapid Searches of Short Words in Genome Sequences", PLoS ONE, 2007, e579, 8 pgs., vol. 2, No. 6.
Jarver et al., "The use of cell-penetrating peptides as a tool for gene regulation", Drug Discovery Today, 2004, pp. 395-402, vol. 9, No. 9.
Jiang et al., "RNA-guided editing of bacterial genomes using CRISPR-Cas systems", Nature Biotechnology, 2013, pp. 233-239, vol. 31, No. 3.
Jiang et al., "The structural biology of CRISPR-Cas systems", Current Opinion in Structural Biology, 2015, pp. 100-111, vol. 30.
Jinek et al., "RNA-programmed genome editing in human cells", eLIFE, 2013, pp. 1-9, vol. 2, e00471.
Kandavelou et al., "Targeted manipulation of mammalian genomes using designed zinc finger nucleases", Biochemical and Biophysical Research Communications, 2009, pp. 56-61, vol. 388.
Katada et al., "Chemical and biological approaches to improve the efficiency of homologous recombination in human cells mediated by artificial restriction DNA cutter", Nucleic Acids Research, 2012, e81, 8 pgs., vol. 40, No. 11.
Kim et al., "Hybrid restriction enzymes; Zinc finger fusions to Fok I cleavage domain", PNAS, 1996, pp. 1156-1160, vol. 93.
Kim et al., "Precision genome engineering with programmable DNA-nicking enzymes", Genome Research, 2012, pp. 1327-1333, vol. 22, No. 7.
Kryukov et al., "A New Database (GCD) on Genome Composition for Eukaryote and Prokaryote Genome Sequences and Their Initial Analyses", Genome Biology and Evolution, 2012, pp. 501-512, vol. 4, No. 4.
Lamartina et al., "Selective Cleavage of AAVS1 Substrates by the Adeno-Associated Virus Type 2 Rep68 Protein Is Dependent on Topological and Sequence Constraints", Journal of Virology, 2000, pp. 8831-8842, vol. 74, No. 19.
Lambowitz et al., "Group II Introns: Mobile Ribozymes that Invade DNA", Cold Spring Harb Perspect Biol, 2011; 3:a003616; 19 pgs.
Lange et al., "Classical Nuclear Localization Signals: Definition, Function, and Interaction with Importin α", The Journal of Biological Chemistry, 2007, pp. 5101-5105, vol. 282, No. 8.
Li et al., "Harnessing Type I and Type III CRISPR-Cas systems for genome editing", Nucleic Acids Research, 2016, e34, pp. 1-12, vol. 44, No. 4.
Lusk et al., "Magnesium and the Growth of *Escherichia coli*", The Journal of Biological Chemistry, 1968, pp. 2618-2624, vol. 243, No. 10.
Mak et al., "TAL effectors: function, structure, engineering and applications", Current Opinion in Structural Biology, 2013, pp. 93-99, vol. 23, No. 1.
Makarova et al., "Unification of Cas protein families and a simple scenario for the origin and evolution of CRISPR-Cas systems", Biology Direct, 2011, pp. 1-27, vol. 6.
Makarova et al., "Evolution and classification of the CRISPR-Cas systems", Nature Review Microbiology, 2011, pp. 467-477, vol. 9, No. 6.
Mali et al., "CAS9 transcriptional activators for target specificity screening and paired nickases for cooperative genome engineering", Nature Biotechnology, 2013, pp. 833-838, vol. 31, No. 9.
Manjunath et al., "Newer Gene Editing Technologies toward HIV Gene Therapy", Viruses, 2013, pp. 2748-2766, vol. 5.
Marraffini et al., "CRISPR interference: RNA-directed adaptive immunity in bacteria and archaea", Nature Reviews, Genetics, 2010, pp. 181-190, vol. 11.
Mastroianni et al., "Group II Intron-Based Gene Targeting Reactions in Eukaryotes", PLoS ONE, 2008, e3121, pp. 1-15, vol. 3, No. 9.
Matsui et al., "Protein Therapy: In Vivo Protein Transduction by Polyarginine (11R) PTD and Subcellular Targeting Delivery", Current Protein and Peptide Science, 2003, pp. 151-157, vol. 4, No. 2.
Miller et al., "An improved zinc-finger nuclease architecture for highly specific genome editing", Nature Biotechnology, 2007, pp. 778-785, vol. 25, No. 7.
Milo et al., "What Are the Concentrations of Different Ions in Cells?", http://book.bionumbers.org/what-are-the-concentrations-of-different-ions-in-cells, printed as pp. 1/5-5/5 on Dec. 20, 2016 from the online version of Cell Biology by the numbers, published Dec. 7, 2015.
Minczuk et al., "Sequence-specific modification of mitochondrial DNA using a chimeric zinc finger methylase", PNAS, 2006, pp. 19689-19694, vol. 103, No. 52.
Mohr et al., "Rules for DNA target-site recognition by a lactococcal group II intron enable retargeting of the intron to specific DNA sequences", Genes & Development, 2000, pp. 559-573, vol. 14.

(56) References Cited

OTHER PUBLICATIONS

Nakamura et al., "Codon usage tabulated from international DNA sequence databases: status for the year 2000", Nucleic Acids Research, 2000, p. 292, vol. 28, No. 1.
Noguchi et al., "Recent Advances in Protein Transduction Technology", Cell Transplantation, 2010, pp. 649-654, vol. 19.
Orlando et al., "Zinc-finger nuclease-driven targeted integration into mammalian genomes using donors with limited chromosomal homology", Nucleic Acids Research, 2010, pp. 1-15, vol. 38, No. 15:e152.
Pabo et al., "Design and Selection of Novel Cyst His2 Zinc Finger Proteins", Annual Review of Biochemistry, 2001, pp. 313-340, vol. 70.
Pattanayak et al., "High-throughput profiling of off-target DNA cleavage reveals RNA-programmed Cas9 nuclease specificity", Nature Biotechnology, 2013, pp. 839-843, vol. 31, No. 9.
Qi et al., "RNA processing enables predictable programming of gene expression", Nature Biotechnology, 2012, pp. 1002-1006, vol. 30, No. 10.
Qi et al., "Repurposing CRISPR as an RNA-Guided Platform for Sequence-Specific Control of Gene Expression", Cell, 2013, pp. 1173-1183, vol. 152, No. 5.
Ramakrishna et al., "Gene disruption by cell-penetrating peptide-mediated delivery of Cas9 protein and guide RNA", Genome Research, 2014, pp. 1020-1027, vol. 24.
Ran et al., "Double Nicking by RNA-Guided CRISPR Cas9 for Enhanced Genome Editing Specificity", Cell, 2013, pp. 1380-1389, vol. 154, No. 6.
Richter et al., "Exploiting CRISPR/Cas: Interference Mechanisms and Applications", International Journal of Molecular Sciences, 2013, pp. 14518-14531, vol. 14.
Romani, "Cellular magnesium homeostasis", Archives of Biochemistry and Biophysics, 2011, pp. 1-23, vol. 512, No. 1.
Ryu et al., "Enhanced Uptake of a Heterologous Protein with an HIV-1 Tat Protein Transduction Domains (PTD) at Both Termini", Molecules and Cells, 2003, pp. 385-391, vol. 16, No. 3.
Sapranauskas et al., "The *Streptococcus thermophilus* CRISPR/Cas system provides immunity in *Escherichia coli*", Nucleic Acids Research, 2011, pp. 9275-9282, vol. 39, No. 21.
Segal et al., "Custom DNA-binding proteins come of age: polydactyl zinc-finger proteins", Current Opinion in Biotechnology, 2001, pp. 632-637, vol. 12.
Shen et al., "Generation of gene-modified mice via Cas9/RNA-mediated gene targeting", Cell Research, 2013, pp. 720-723, vol. 23, No. 5.
Sigma-Aldrich Product Information, Custom CRISPR Plasmid, 2013, 5 pgs.
Szczepek et al., "Structure-based redesign of the dimerization interface reduces the toxicity of zinc-finger nucleases", Nature Biotechnology, 2007, pp. 786-793, vol. 25, No. 7.
Truong et al., "Enhanced group II intron retrohoming in magnesium-deficient *Escherichia coli* via selection of mutations in the ribozyme core", PNAS, 2013, pp. E3800-E3809, vol. 110, No. 40.
Wang et al., "One-Step Generation of Mice Carrying Mutations in Multiple Genes by CRISPR/Cas-Mediated Genome Engineering", Cell, 2013, pp. 910-918, vol. 153.
Wiedenheft et al., "RNA-guided genetic silencing systems in bacteria and archaea", Nature, 2012, pp. 331-338, vol. 482.
Zhang et al., "Synthetic Zinc Finger Transcription Factor Action at an Endogenous Chromosomal Site: Activation of the Human Erythropoietin Gene", The Journal of Biological Chemistry, 2000, pp. 33850-33860, vol. 275, No. 43.
Zhang et al., "MDV-1 VP22: a transporter that can selectively deliver proteins into cells", Archives of Virology, 2009, pp. 1027-1034, vol. 154, No. 7.
International Search Report and Written Opinion from International Application No. PCT/US2017/018589, dated May 9, 2017; 15 pgs.
Bolukbasi et al., "DNA-binding-domain fusions enhance the targeting range and precision of Cas9", Nature Methods, 2015, pp. 1150-1156 and Supplemental Materials, vol. 12, No. 12.
Chen et al., "Targeted activation of diverse CRISPR-Cas systems for mammalian genome editing via proximal CRISPR targeting", Nature Communications, Article No. 14958 (2017), doi:10.1038/ncomms14958, pp. 1-12.
Horlbeck et al., "Nucleosomes impede Cas9 access to DNA in vivo and in vitro", eLIFE, 2016, e12677, pp. 1-21, vol. 5.
Index; Keystone Symposia on Molecular and Cellular Biology, "Precision Genome Engineering (A2)"; Breckenridge, Colorado, Jan. 8-12, 2017; 3 pgs.
Polstein et al., "Genome-wide specificity of DNA binding, gene regulation, and chromatin remodeling by TALE- and CRISPR/Cas9-based transcriptional activators", Genome Research, 2015, pp. 1158-1169, vol. 25.
Invitation pursuant to Rule 63(1) EPC from related European Application No. 17157024.5, dated Sep. 26, 2017; 3 pgs.
Anonymous, "Using Cpf1 for CRISPR . Benchling", Jan. 1, 2015; pp. 1-4, XP55396832, Retrieved from the Internet: URL:https://benchling.com/pub/cpf1 [retrieved Aug. 8, 2017].
Chen et al., "Improving CRISPR Gene Editing Efficiency by Proximal dCas9 Targeting", bio-protocol, 2017, pp. 1-9, vol. 7, No. 15.
Chen et al. "Supplementary Information: Targeted activation of diverse CRISPR-Cas systems for mammalian genome editing via proximal CRISPR targeting", Nature Communications, vol. 8, No. 14958, Apr. 7, 2017, pp. 1-18.
Fagerlund et al., "The Cpf1 CRISPR-Cas protein expands genome-editing tools", Genome Biology, 2015, pp. 1-3, vol. 16.
Fonfara et al., "The CRISPR-associated DNA-cleaving enzyme Cpf1 also processes precursor CRISPR RNA", Nature, 2016, pp. 517-521, vol. 532.
Richardson et al., "Enhancing homology-directed genome editing by catalytically active and inactive CRISPR-Cas9 using asymmetric donor DNA", Nature Biotechnology, 2016, pp. 339-344, vol. 34, No. 3.
Richardson et al., "Supplementary Information: Enhancing homology-directed genome editing by catalytically active and inactive CRISPR-Cas9 using asymmetric donor DNA", Nature Biotechnology, 2016, vol. 34, No. 3, 108 pgs.
Partial European Search Report from related European Application No. EP17157024.5, dated Jan. 2, 2018; 18 pgs.
Horlbeck et al., "Compact and highly active next-generation libraries for CRISPR-mediated gene repression and activation", eLIFE, 2016, e19760, pp. 1-20, vol. 5.
Price et al., "Cas9-mediated targeting of viral RNA in eukaryotic cells", PNAS, 2015, pp. 6164-6169, vol. 112, No. 19.
Combined Search and Examination Report from related Application No. GB1702743.4, dated Dec. 8, 2017; 6 pgs.

\* cited by examiner

FIG. 6

SEQUENCE LISTING

```
<160> NUMBER OF SEQ ID NOS: 49

<210> SEQ ID NO 1
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 1

Pro Lys Lys Lys Arg Lys Val
1               5

<210> SEQ ID NO 2
<211> LENGTH: 7
<212> TYPE: PRT
<213> ORGANISM: Artificial Sequence
```

```
<220> FEATURE:
<223> OTHER INFORMATION: SYNTHESIZED

<400> SEQUENCE: 2

Pro Lys Lys Lys Arg Arg Val
1               5

<210> SEQ ID NO 3
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 4

Gly Arg Lys Lys Arg Arg Gln Arg Arg Arg Pro Pro Gln Pro Lys Lys
1               5                   10                  15

Lys Arg Lys Val
            20

<210> SEQ ID NO 5
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 5

Pro Leu Ser Ser Ile Phe Ser Arg Ile Gly Asp Pro Pro Lys Lys Lys
1               5                   10                  15

Arg Lys Val

<210> SEQ ID NO 6
<211> LENGTH: 24
<212> TYPE: PRT
<213> ORGANISM: Artificial Sequence
<220> FEATURE:
<223> OTHER INFORMATION: SYNTHESIZED

<400> SEQUENCE: 6

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 7
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 7

Gly Ala Leu Phe Leu Gly Phe Leu Gly Ala Ala Gly Ser Thr Met Gly
```

```
                1               5                  10                    15
Ala Trp Ser Gln Pro Lys Lys Lys Arg Lys Val
                20                  25
```

<210> SEQ ID NO 8
<211> LENGTH: 21
<212> TYPE: PRT
<213> ORGANISM: Artificial Sequence
<220> FEATURE:
<223> OTHER INFORMATION: SYNTHESIZED

<400> SEQUENCE: 8

```
Lys Glu Thr Trp Trp Glu Thr Trp Trp Thr Glu Trp Ser Gln Pro Lys
1               5                   10                  15
Lys Lys Arg Lys Val
            20
```

<210> SEQ ID NO 9
<211> LENGTH: 21
<212> TYPE: DNA
<213> ORGANISM: Artificial Sequence
<220> FEATURE:
<223> OTHER INFORMATION: SYNTHESIZED

<400> SEQUENCE: 9
ctcccctgct tcttgtcgta t                                    21

<210> SEQ ID NO 10
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 10
acaggtcgtg gacactcaca                                      20

<210> SEQ ID NO 11
<211> LENGTH: 23
<212> TYPE: DNA
<213> ORGANISM: Artificial Sequence
<220> FEATURE:
<223> OTHER INFORMATION: SYNTHESIZED

<400> SEQUENCE: 11
cggctgtcat cacttagacc tca                                  23

<210> SEQ ID NO 12
<211> LENGTH: 24
<212> TYPE: DNA
<213> ORGANISM: Artificial Sequence
<220> FEATURE:
<223> OTHER INFORMATION: SYNTHESIZED

<400> SEQUENCE: 12
gcagcctaag ggtgggaaaa taga                                 24

<210> SEQ ID NO 13
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 13
agggcaagtt aagggaatag tggaa                                        25

<210> SEQ ID NO 14
<211> LENGTH: 25
<212> TYPE: DNA
<213> ORGANISM: Artificial Sequence
<220> FEATURE:
<223> OTHER INFORMATION: SYNTHESIZED

<400> SEQUENCE: 14
ccaagggtag accaccagta atctg                                        25

<210> SEQ ID NO 15
<211> LENGTH: 101
<212> TYPE: DNA
<213> ORGANISM: Homo sapiens

<400> SEQUENCE: 15
cctttccagc attcgccagt acgagcttgt ggtccacacc gacatagatg cggccaaggt    60
gtacatgggg gagatgggcc ggctgaagag ctacgagaac c                      101

<210> SEQ ID NO 16
<211> LENGTH: 101
<212> TYPE: DNA
<213> ORGANISM: Homo sapiens

<400> SEQUENCE: 16
ggttctcgta gctcttcagc cggcccatct cccccatgta caccttggcc gcatctatgt    60
cggtgtggac acaagctcg tactggcgaa tgctggaaag g                       101

<210> SEQ ID NO 17
<211> LENGTH: 105
<212> TYPE: DNA
<213> ORGANISM: Homo sapiens

<400> SEQUENCE: 17
ccgcttcccg gcctcaccct tggtctcccc tttccagcat tcgccagtac gagcttgtgg    60
tccacaccga catagatgcg gccaaggtgt acatggggga gatgg                  105

<210> SEQ ID NO 18
<211> LENGTH: 105
<212> TYPE: DNA
<213> ORGANISM: Homo sapiens

<400> SEQUENCE: 18
ccatctcccc catgtacacc ttggccgcat ctatgtcggt gtggaccaca agctcgtact    60
ggcgaatgct ggaaagggga gaccaagggt gaggccggga agcgg                  105

<210> SEQ ID NO 19
<211> LENGTH: 110
<212> TYPE: DNA
<213> ORGANISM: Homo sapiens

<400> SEQUENCE: 19
ccgcttcccg gcctcaccct tggtctcccc tttccagcat tcgccagtac gagcttgtgg    60
tccacaccga catagatgcg gccaaggtgt acatggggga gatgggccgg             110

<210> SEQ ID NO 20
<211> LENGTH: 110
<212> TYPE: DNA
<213> ORGANISM: Homo sapiens

<400> SEQUENCE: 20
ccggcccatc tcccccatgt acaccttggc cgcatctatg tcggtgtgga ccacaagctc    60
gtactggcga atgctggaaa ggggagacca agggtgaggc cgggaagcgg              110

<210> SEQ ID NO 21
<211> LENGTH: 117
<212> TYPE: DNA
<213> ORGANISM: Homo sapiens

<400> SEQUENCE: 21
tcgactgttg cttacacttt cttctgacat aacagtgttc actagcaacc tcaaacagac    60
accatggtgc atctgactcc tgaggagaag actgctgtca atgccctgtg gggcaaa     117

<210> SEQ ID NO 22
<211> LENGTH: 117
<212> TYPE: DNA
<213> ORGANISM: Homo sapiens

<400> SEQUENCE: 22
gaacggggtg tcccgtcatt gccgtctgaa gaggagtcct cagtctacgt ggtaccacag    60
acaaactcca acgatcactt gtgtcaacac agtcttcgtt tacattcgtt atctacc    117

<210> SEQ ID NO 23
<211> LENGTH: 142
<212> TYPE: DNA
<213> ORGANISM: Homo sapiens
<220> FEATURE:
<221> NAME/KEY: misc_feature
<222> LOCATION: (74)..(113)
<223> OTHER INFORMATION: n is a, c, g, or t

<400> SEQUENCE: 23
tgtacatggg ggagatgggc cggctgaaga gctacgagaa ccagaagccg tgagtggagg    60
gagcgtggct tggnnnnnnn nnnnnnnnnn nnnnnnnnnn nnnnnnnnnn nnntctgccg   120
tgtatcccca tatccccaca gg                                           142

<210> SEQ ID NO 24
<211> LENGTH: 142
<212> TYPE: DNA
<213> ORGANISM: Homo sapiens
<220> FEATURE:
<221> NAME/KEY: misc_feature
<222> LOCATION: (30)..(69)
<223> OTHER INFORMATION: n is a, c, g, or t

<400> SEQUENCE: 24
cctgtgggga tatggggata cacggcagan nnnnnnnnnn nnnnnnnnnn nnnnnnnnnn    60
nnnnnnnnnc caagccacgc tccctccact cacggcttct ggttctcgta gctcttcagc   120
cggcccatct cccccatgta ca                                           142

<210> SEQ ID NO 25
<211> LENGTH: 47
<212> TYPE: DNA
<213> ORGANISM: Homo sapiens

<400> SEQUENCE: 25
cagggatcct gtgtcccga gctgggacca ccttatattc ccagggc                  47

<210> SEQ ID NO 26

-continued

```
<211> LENGTH: 47
<212> TYPE: DNA
<213> ORGANISM: Homo sapiens

<400> SEQUENCE: 26
gccctggcaa tataaggtgg tcccagctcg gggacacagg atccctg        47

<210> SEQ ID NO 27
<211> LENGTH: 88
<212> TYPE: DNA
<213> ORGANISM: Artificial Sequence
<220> FEATURE:
<223> OTHER INFORMATION: SYNTHESIZED

<400> SEQUENCE: 27 caccettggt ctcccctttc cagcattcgc cagtacgagc gaattcttgt ggtccacacc    60
gacatagatg cggccaaggt gtacatgg                                      88

<210> SEQ ID NO 28
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 28

Tyr Gly Arg Lys Lys Arg Arg Gln Arg Arg Arg
1               5                   10

<210> SEQ ID NO 29
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 29

Arg Lys Lys Arg Arg Gln Arg Arg Arg
1               5

<210> SEQ ID NO 30
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 30

Pro Ala Ala Lys Arg Val Lys Leu Asp
1               5

<210> SEQ ID NO 31
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 31

Arg Gln Arg Arg Asn Glu Leu Lys Arg Ser Pro
1               5                   10

<210> SEQ ID NO 32
<211> LENGTH: 8
<212> TYPE: PRT
<213> ORGANISM: Artificial Sequence
```

```
<220> FEATURE:
<223> OTHER INFORMATION: SYNTHESIZED

<400> SEQUENCE: 32

Val Ser Arg Lys Arg Pro Arg Pro
1               5

<210> SEQ ID NO 33
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 33

Pro Pro Lys Lys Ala Arg Glu Asp
1               5

<210> SEQ ID NO 34
<211> LENGTH: 8
<212> TYPE: PRT
<213> ORGANISM: Artificial Sequence
<220> FEATURE:
<223> OTHER INFORMATION: SYNTHESIZED

<400> SEQUENCE: 34

Pro Gln Pro Lys Lys Lys Pro Leu
1               5

<210> SEQ ID NO 35
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 35

Ser Ala Leu Ile Lys Lys Lys Lys Lys Met Ala Pro
1               5                   10

<210> SEQ ID NO 36
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 36

Pro Lys Gln Lys Lys Arg Lys
1               5

<210> SEQ ID NO 37
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 37

Arg Lys Leu Lys Lys Lys Ile Lys Lys Leu
1               5                   10

<210> SEQ ID NO 38
<211> LENGTH: 10
<212> TYPE: PRT
<213> ORGANISM: Artificial Sequence
<220> FEATURE:
```

```
<223> OTHER INFORMATION: SYNTHESIZED

<400> SEQUENCE: 38

Arg Glu Lys Lys Lys Phe Leu Lys Arg Arg
1               5                   10

<210> SEQ ID NO 39
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 39

Lys Arg Lys Gly Asp Glu Val Asp Gly Val Asp Glu Val Ala Lys Lys
1               5                   10                  15

Lys Ser Lys Lys
            20

<210> SEQ ID NO 40
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 40

Arg Lys Cys Leu Gln Ala Gly Met Asn Leu Glu Ala Arg Lys Thr Lys
1               5                   10                  15

Lys

<210> SEQ ID NO 41
<211> LENGTH: 38
<212> TYPE: PRT
<213> ORGANISM: Artificial Sequence
<220> FEATURE:
<223> OTHER INFORMATION: SYNTHESIZED

<400> SEQUENCE: 41

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 42
<211> LENGTH: 42
<212> TYPE: PRT
<213> ORGANISM: Artificial Sequence
<220> FEATURE:
<223> OTHER INFORMATION: SYNTHESIZED

<400> SEQUENCE: 42

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 43
<211> LENGTH: 11
```

```
<212> TYPE: PRT
<213> ORGANISM: Artificial Sequence
<220> FEATURE:
<223> OTHER INFORMATION: SYNTHESIZED

<400> SEQUENCE: 43

Tyr Ala Arg Ala Ala Ala Arg Gln Ala Arg Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 44

Thr His Arg Leu Pro Arg Arg Arg Arg Arg Arg
1               5                   10

<210> SEQ ID NO 45
<211> LENGTH: 11
<212> TYPE: PRT
<213> ORGANISM: Artificial Sequence
<220> FEATURE:
<223> OTHER INFORMATION: SYNTHEISZED

<400> SEQUENCE: 45

Gly Gly Arg Arg Ala Arg Arg Arg Arg Arg Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 46

Arg Arg Gln Arg Arg Thr Ser Lys Leu Met Lys Arg
1               5                   10

<210> SEQ ID NO 47
<211> LENGTH: 27
<212> TYPE: PRT
<213> ORGANISM: Artificial Sequence
<220> FEATURE:
<223> OTHER INFORMATION: SYNTHESIZED

<400> SEQUENCE: 47

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 48
<211> LENGTH: 33
<212> TYPE: PRT
<213> ORGANISM: Artificial Sequence
<220> FEATURE:
<223> OTHER INFORMATION: SYNTHESIZED

<400> SEQUENCE: 48

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
```

```
                20                  25                  30
Ala

<210> SEQ ID NO 49
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 49

Arg Gln Ile Lys Ile Trp Phe Gln Asn Arg Arg Met Lys Trp Lys Lys
1               5                   10                  15
```

USING PROGRAMMABLE DNA BINDING PROTEINS TO ENHANCE TARGETED GENOME MODIFICATION

CROSS-REFERENCE TO RELATED APPLICATIONS

This application claims priority to U.S. Provisional Application Ser. No. 62/344,858, filed Jun. 2, 2016, and U.S. Provisional Application Ser. No. 62/358,415, filed Jul. 5, 2016, the disclosure of each is hereby incorporated by reference in its entirety.

FIELD

The present disclosure relates to compositions and methods for increasing the efficiency and/or specificity of targeted genome modification.

SEQUENCE LISTING

The instant application contains a Sequence Listing which has been submitted electronically in ASCII text format and is hereby incorporated by reference in its entirety. Said ASCII copy of the sequence listing, which was created on Feb. 7, 2017, is named 561367_SequenceListing_ST25.TXT and is 11,964 bytes in size.

BACKGROUND

Programmable endonucleases have increasingly become an important tool for targeted genome engineering or modification in eukaryotes. Recently, RNA-guided clustered regularly interspersed short palindromic repeats (CRISPR)/CRISPR-associated (Cas) (CRISPR/Cas) systems have emerged as a new generation of genome modification tools. These new programmable endonucleases have greatly improved the genome editing capability compared to previous generations of nucleases such as zinc finger nucleases (ZFNs) and transcription activator-like effector nucleases (TALENs).

However, not all genomic targets are accessible to efficient modification by these programmable endonucleases. In fact, some CRISPR-Cas endonucleases appear to have little or no activity in human cells. Among other things, chromatin structure may present a barrier to these programmable endonucleases and prevent them from binding the target sequence. Thus, there is a need for improving accessibility of these programmable endonucleases to target sequences and/or improving the efficiency of targeted genome modification. Moreover, there is a need for increasing the specificity to targeted genome modification by reducing off-target effects.

SUMMARY

Among the various aspects of the present disclosure is a composition comprising (a) a programmable DNA modification protein or nucleic acid encoding the programmable DNA modification protein and (b) at least one programmable DNA binding protein or nucleic acid encoding the at least one programmable DNA binding protein. In general, the programmable DNA modification protein has nuclease activity (i.e., cleaves both strands of a double-stranded sequence) or non-nuclease activity (e.g., epigenetic modification activity or transcriptional regulation activity) and the at least one programmable DNA binding protein lacks nuclease activity.

In embodiments in which the programmable DNA modification protein has nuclease activity, for example, the programmable DNA modification protein can be selected from a RNA-guided clustered regularly interspersed short palindromic repeats (CRISPR)/CRISPR-associated (Cas) (CRISPR/Cas) nuclease system, a CRISPR/Cas dual nickase system, a zinc finger nuclease (ZFN), a transcription activator-like effector nuclease (TALEN), a meganuclease, a fusion protein comprising a programmable DNA binding domain linked to a nuclease domain (i.e., generates a double-stranded DNA break), and combinations thereof.

In embodiments in which the programmable DNA modification protein has non-nuclease activity, for example, the programmable DNA modification protein can be a fusion protein comprising a programmable DNA binding domain linked to a non-nuclease modification domain. In certain embodiments, the programmable DNA binding domain of the fusion protein can be catalytically inactive CRISPR/Cas system, a catalytically inactive meganuclease, a zinc finger protein, or a transcription activator-like effector, and the non-nuclease modification domain of the fusion protein can have acetyltransferase activity, deacetylase activity, methyltransferase activity, demethylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, citrullination activity, helicase activity, amination activity, deamination activity, alkylation activity, dealkylation activity, oxidation activity, transcriptional activation activity, or transcriptional repressor activity. In specific embodiments, the non-nuclease modification domain of the fusion protein has cytosine deaminase activity, histone acetyltransferase activity, transcriptional activation activity, or transcriptional repressor activity.

In accordance with certain embodiments of the compositions disclosed herein, the at least one programmable DNA binding protein can be a catalytically inactive CRISPR/Cas system, a catalytically inactive meganuclease, a zinc finger protein, a transcription activator-like effector, a CRISPR/Cas nickase, a ZFN nickase, a TALEN nickase, or a meganuclease nickase.

In general, nucleic acid encoding the programmable DNA modification protein and/or the at least one programmable DNA binding protein is mRNA or DNA. In some embodiments the nucleic acid encoding the programmable DNA modification protein and/or the at least one programmable DNA binding protein is part of a vector such as, for example, a plasmid vector, a lentiviral vector, an adeno-associated viral vector, or an adenoviral vector.

In specific embodiments, the programmable DNA modification protein comprises a CRISPR/Cas nuclease system, a CRISPR/Cas dual nickase system, or a catalytically inactive CRISPR/Cas system linked to a non-nuclease domain, and the at least one programmable DNA binding protein comprises a catalytically inactive CRISPR/Cas system, wherein each CRISPR/Cas system comprises a CRISPR/Cas protein and a guide RNA. In various embodiments, each CRISPR/Cas nuclease system can be a type I CRISPR/Cas system, a type II CRISPR/Cas system, a type III CRISPR/Cas system, or a type V CRISPR/Cas system. In some embodiments, each guide RNA can be at least partially chemically synthesized. In other embodiments, each guide RNA can be enzymatically synthesized. In further embodiments, nucleic acid encoding each CRISPR/Cas protein can be mRNA, and nucleic acid encoding each guide RNA can be DNA. In still other embodiments, nucleic acid encoding each CRISPR/Cas protein can be mRNA, and nucleic acid encoding each guide RNA can be DNA. In certain aspects, nucleic acid encoding the CRISPR/Cas protein and/or nucleic acid encoding the guide RNA can be part of a vector, for example, a plasmid vector, a lentiviral vector, an adeno-associated viral vector, or an adenoviral vector.

Another aspect of the present disclosure encompasses kits comprising any one or more of the compositions detailed above.

Still another aspect of the present disclosure provides methods for increasing targeted genome modification efficiency and/or specificity in a eukaryotic cell. The methods involve introducing into a eukaryotic cell (a) a programmable DNA modification protein or nucleic acid encoding the programmable DNA modification protein and (b) at least one programmable DNA binding protein or nucleic acid encoding the at least one programmable DNA binding protein. The programmable DNA modification protein is targeted to a target chromosomal sequence and each of the at least one programmable DNA binding proteins is targeted to a site proximal to the target chromosomal sequence. Binding of the at least one programmable DNA binding protein to the site proximal to the target chromosomal sequence increases accessibility of the programmable DNA modification protein to the target chromosomal sequence, thereby increasing targeted genome modification efficiency and/or specificity. The proximal site bound by each of the at least one programmable DNA binding protein is located, for example, within about 250 base pairs on either side of the target chromosomal sequence. In some embodiments, the proximal binding site(s) is located less than about 200 bp or less than about 100 bp on either side of the target chromosomal sequence.

The programmable DNA modification protein used in the method can be a CRISPR/Cas nuclease system, a CRISPR/Cas dual nickase system, a zinc finger nuclease (ZFN), a transcription activator-like effector nuclease (TALEN), a meganuclease, a fusion protein comprising a programmable DNA binding domain linked to a nuclease domain, or a fusion protein comprising a programmable DNA binding domain linked to a non-nuclease domain. The programmable DNA binding domain of the fusion protein can be a catalytically inactive CRISPR/Cas system, a catalytically inactive meganuclease, a zinc finger protein, or a transcription activator-like effector, and the non-nuclease modification domain of the fusion protein can have acetyltransferase activity, deacetylase activity, methyltransferase activity, demethylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, citrullination activity, helicase activity, amination activity, deamination activity, alkylation activity, dealkylation activity, oxidation activity, transcriptional activation activity, or transcriptional repressor activity. In specific embodiments, the non-nuclease modification domain of the fusion protein has cytosine deaminase activity, histone acetyltransferase activity, transcriptional activation activity, or transcriptional repressor activity.

The at least one programmable DNA binding protein used in the method binds DNA but lacks nuclease activity (i.e., double strand cleavage activity). In certain embodiments, the least one programmable DNA binding protein can be a catalytically inactive CRISPR/Cas system, a catalytically inactive meganuclease, a zinc finger protein, a transcription activator-like effector, a CRISPR/Cas nickase, a ZFN nickase, a TALEN nickase, or a meganuclease nickase.

In specific embodiments, the programmable DNA modification protein comprises a CRISPR/Cas nuclease system, a CRISPR/Cas dual nickase system, or a catalytically inactive CRISPR/Cas system linked to a non-nuclease domain, and the at least one programmable DNA binding protein comprises a catalytically inactive CRISPR/Cas system, wherein each CRISPR/Cas system comprises a CRISPR/Cas protein and a guide RNA.

In various embodiments, at least two, at least three, or more than three programmable DNA binding proteins are introduced into the eukaryotic cell. In specific embodiments, the eukaryotic cell is a mammalian cell, or a human cell.

A further aspect of the present disclosure encompasses methods for detecting a chromosomal sequence or genomic locus in a eukaryotic cell. The methods involve introducing into the eukaryotic cell (a) a programmable DNA binding protein comprising at least one detectable marker domain or nucleic acid encoding the programmable DNA binding protein comprising at least one detectable marker domain and (b) at least one programmable DNA binding protein or nucleic acid encoding the at least one programmable DNA binding protein, wherein the programmable DNA binding protein comprising at least one detectable marker domain is targeted to a target chromosomal sequence and each of the at least one programmable DNA binding protein is targeted to a site proximal to the target chromosomal sequence, wherein binding of the at least one programmable DNA binding protein to the site proximal to the target chromosomal sequence increases accessibility of the programmable DNA binding protein comprising at least one detectable marker domain to the target chromosomal sequence. The methods can further involve detecting the programmable DNA binding protein comprising at least one detectable marker domain bound to the target chromosomal sequence. The detecting step can be in live cells or fixed cells and can involve, for example, dynamic live cell imaging, fluorescent microscopy, confocal microscopy, immunofluorescence, immunodetection, RNA-protein binding, or protein-protein binding.

The programmable DNA binding protein comprising at least one detectable marker domain that is used in the detection method comprises a programmable DNA binding domain, which can be a catalytically inactive CRISPR/Cas system, a catalytically inactive meganuclease, a zinc finger protein, or a transcription activator-like effector. The at least one detectable marker domain of the programmable DNA binding protein comprising at least one detectable marker domain can be, for example, a fluorescent protein, a fluorescent tag, an epitope tag, or a naturally occurring epitope within the programmable DNA binding protein. In some embodiments, the programmable DNA binding protein comprising at least one detectable marker domain can further comprise a non-nuclease modification. The at least one programmable DNA binding protein binds DNA but lacks nuclease activity (i.e., double strand cleavage activity). In some embodiments, the programmable DNA binding protein can be a catalytically inactive CRISPR/Cas system, a catalytically inactive meganuclease, a zinc finger protein, a transcription activator-like effector, a CRISPR/Cas nickase, a ZFN nickase, a TALEN nickase, or a meganuclease nickase. In specific embodiments, the programmable DNA binding protein comprising at least one detectable marker domain can be a catalytically inactive CRISPR/Cas system linked to at least one detectable marker domain, and the at least one programmable DNA binding protein can be a catalytically inactive CRISPR/Cas system.

Other aspects and features of the disclosure are detailed below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 illustrates that the binding of catalytically inactive SpCas9 (SpdCas9) to proximal site(s) increases the specific cleavage by CjCas9. The target sites of CjCas9 in the HBD and HBB loci, as well as the binding sites of SpdCas9 in the HBB locus, are shown at the top. The results of a Cel-I nuclease assay are shown at the bottom.

DETAILED DESCRIPTION

Figure 1:
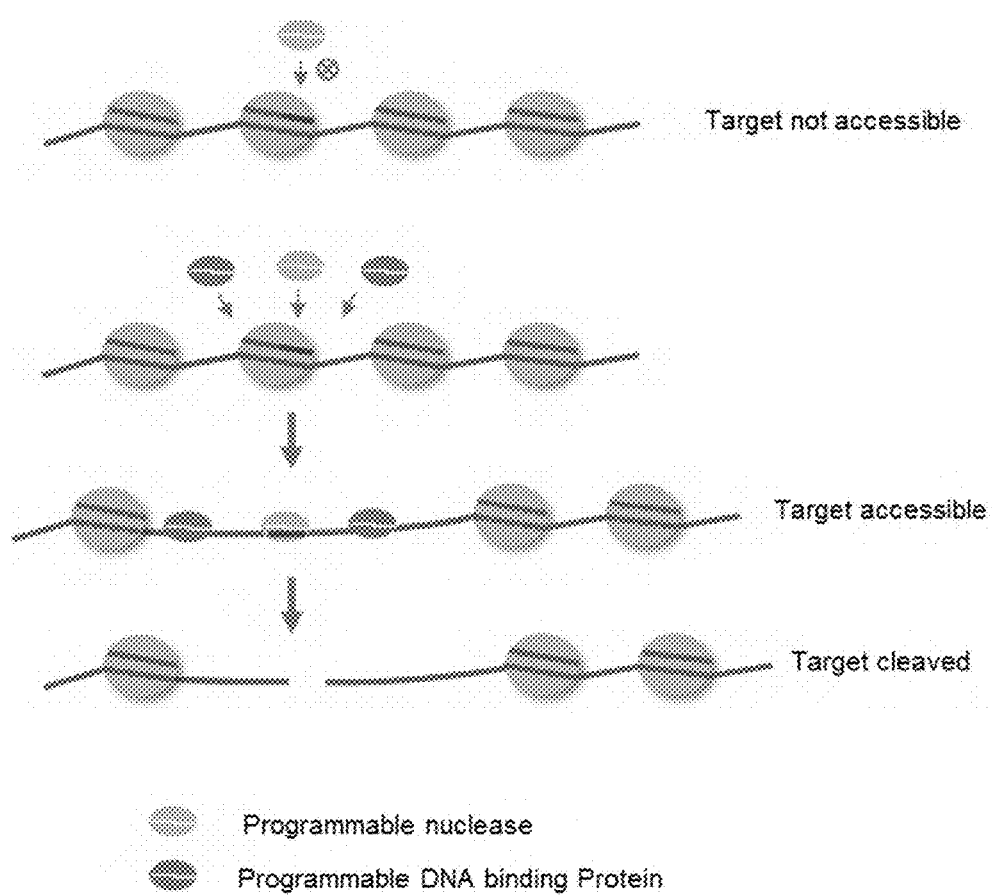
FIG. 1 provides a diagram of one embodiment of the methods disclosed herein. Proximal binding of programmable DNA binding protein(s) increases the accessibility of the target site to a programmable nuclease, thereby increasing the efficiency of cleavage at the target site.

The present disclosure provides compositions and methods for increasing the accessibility of chromosomal DNA to targeting endonucleases and other programmable DNA modification proteins, wherein the increased accessibility leads to increased efficiency and/or specificity of targeted genome modification or epigenetic modification. It has been found that some CRISPR/Cas endonucleases have reduced or no activity in human cells. It is possible that nucleosome occupancy, positioning, and how a DNA sequence is wrapped around the histone octamer can determine how accessible the sequence is to a DNA binding protein (Chereji et al., Briefing Functional Genomics, 2014, 14:506-60). Thus, it is possible that the hindrance imposed by local chromatin configuration may play a role in the apparent inactivity of many CRISPR/Cas endonucleases in human cells. It has been discovered, as detailed herein, that the binding of DNA binding proteins to sites located proximal (i.e., within about 250 base pairs) to the target site of a targeting DNA modification protein increases the accessibility of the targeting DNA modification protein to the target site, thereby increasing the efficiency and/or specificity of targeted genome modification or targeted epigenetic modification. The compositions and methods disclosed herein, therefore, enable efficient targeted genome modification/epigenetic modification using CRISPR/Cas endonucleases previously thought to be inactive in human cells. Moreover, the compositions and methods disclosed herein also improve selective genome modification between nearly identical target sties, thereby reducing off-target effects.

(I) Compositions

One aspect of the present disclosure provides compositions comprising (a) programmable DNA modification proteins or nucleic acid encoding the programmable DNA modification proteins and (b) at least one programmable DNA binding protein or nucleic acid encoding the at least one programmable DNA binding protein. Programmable DNA modification proteins are detailed below in section (I)(a), programmable DNA binding proteins are detailed below in section (I)(b), and nucleic acids encoding these proteins are detailed below in section (I)(c).

(a) Programmable DNA Modification Proteins

A programmable DNA modification protein is a protein that binds to a specific target sequence in chromosomal DNA and modifies the DNA or a protein associated with the DNA at or near the target sequence. Thus, a programmable DNA modification protein comprises a DNA binding domain and a catalytically active modification domain.

The DNA binding domain is programmable, in that it can be designed or engineered to recognize and bind different DNA sequences. In some embodiments, for example, the DNA binding is mediated by interaction between the protein and the target DNA. Thus, the DNA binding domain can be programmed to bind a DNA sequence of interest by protein engineering. In other embodiments, for example, DNA binding is mediated by a guide RNA that interacts with the programmable DNA binding domain of the protein and the target DNA. In such instances, the programmable DNA binding domain can be targeted to a DNA sequence of interest by designing the appropriate guide RNA.

A variety of modification domains can be included in the programmable DNA modification proteins. In some embodiments, the modification domain is a nuclease domain, which has nuclease activity and cleaves both strands of a double-stranded DNA sequence (i.e., generates a double-stranded break). The double-stranded break can then be repaired by a cellular DNA repair process such as non-homologous end-joining (NHEJ) or homology-directed repair (HDR). As a consequence, the DNA sequence can be modified by a deletion, insertion, and/or substitution of at least one base pair up to, for instance, many thousands of base pairs. Examples of programmable DNA modification proteins comprising nuclease domains include, without limit, CRISPR/Cas nuclease systems, CRISPR/Cas dual nickase systems, zinc finger nucleases, transcription activator-like effector nucleases, meganucleases, fusion proteins comprising a nuclease domain linked to a programmable DNA binding domain, and combinations thereof. Programmable DNA modification proteins comprising nuclease domains are detailed below in sections (I)(a)(i)-(vi).

In other embodiments, the modification domain of the programmable DNA modification protein has non-nuclease activity (e.g., epigenetic modification activity or transcriptional regulation activity) such that the programmable DNA modification protein modifies the structure and/or activity of the DNA and/or protein(s) associated with the DNA. Thus, the programmable DNA modification protein is a fusion protein comprising a non-nuclease modification domain linked to a programmable DNA binding domain. Such proteins are detailed below in section (I)(a)(vii).

The programmable DNA modification proteins can comprise wild-type or naturally-occurring DNA binding and/or modification domains, modified versions of naturally-occurring DNA binding and/or modification domains, synthetic or artificial DNA binding and/or modification domains, and combinations thereof.

(i) CRISPR/Cas Nuclease Systems

In some embodiments, the programmable DNA modification protein can be a RNA-guided CRISPR/Cas nuclease system, which introduces a double-stranded break in the DNA. The CRISPR/Cas nuclease system comprises a CRISPR/Cas nuclease and a guide RNA.

CRISPR/Cas Nuclease.

In certain embodiments, the CRISPR/Cas nuclease can be derived from a type I (i.e., IA, IB, IC, ID, IE, or IF), type II (i.e., IIA, IIB, or IIC), type III (i.e., IIIA or IIIB), or type V CRISPR system, which are present in various bacteria and archaea. For example, the CRISPR/Cas system can be from *Streptococcus* sp. (e.g., *Streptococcus pyogenes*), *Campylobacter* sp. (e.g., *Campylobacter jejuni*), *Francisella* sp. (e.g., *Francisella novicida*), *Acaryochloris* sp., *Acetohalobium* sp., *Acidaminococcus* sp., *Acidithiobacillus* sp., *Alicyclobacillus* sp., *Allochromatium* sp., *Ammonifex* sp., *Anabaena* sp., *Arthrospira* sp., *Bacillus* sp., *Burkholderiales* sp., *Caldicelulosiruptor* sp., *Candidatus* sp., *Clostridium* sp., *Crocosphaera* sp., *Cyanothece* sp., *Exiguobacterium* sp., *Finegoldia* sp., *Ktedonobacter* sp., *Lachnospiraceae* sp., *Lactobacillus* sp., *Lyngbya* sp., *Marinobacter* sp., *Methanohalobium* sp., *Microscilla* sp., *Microcoleus* sp., *Microcystis* sp., *Natranaerobius* sp., *Neisseria* sp., *Nitrosococcus* sp., *Nocardiopsis* sp., *Nodularia* sp., *Nostoc* sp., *Oscillatoria* sp., *Polaromonas* sp., *Pelotomaculum* sp., *Pseudoalteromonas* sp., *Petrotoga* sp., *Prevotella* sp., *Staphylococcus* sp., *Streptomyces* sp., *Streptosporangium* sp., *Synechococcus* sp., *Thermosipho* sp., or *Verrucomicrobia* sp. In still other embodiments, the CRISPR/Cas nuclease can be derived from an archaeal CRISPR system, a CRISPR-CasX system, or a CRISPR-CasY system (Burstein et al., Nature, 2017, 542(7640):237-241).

In one particular embodiment, the CRISPR/Cas nuclease can be derived from a type I CRISPR/Cas system. In another particular embodiment, the CRISPR/Cas nuclease can be derived from a type II CRISPR/Cas system. In another particular embodiment, the CRISPR/Cas nuclease can be derived from a type III CRISPR/Cas system. In another particular embodiment, the CRISPR/Cas nuclease can be derived from a type V CRISPR/Cas system.

Non-limiting examples of suitable CRISPR proteins include Cas proteins, Cpf proteins, C2c proteins (e.g., C2c1, C2c2, Cdc3), Cmr proteins, Csa proteins, Csb proteins, Csc proteins, Cse proteins, Csf proteins, Csm proteins, Csn proteins, Csx proteins, Csy proteins, Csz proteins, and derivatives or variants thereof. In specific embodiments, the CRISPR/Cas nuclease can be a type II Cas9 protein, a type V Cpf1 protein, or a derivative thereof.

In some embodiments, the CRISPR/Cas nuclease can be *Streptococcus pyogenes* Cas9 (SpCas9) or *Streptococcus thermophilus* Cas9 (StCas9). In other embodiments, the CRISPR/Cas nuclease can be *Campylobacter jejuni* Cas9 (CjCas9). In alternate embodiments, the CRISPR/Cas nuclease can be *Francisella novicida* Cas9 (FnCas9). In still other embodiments, the CRISPR/Cas nuclease can be *Neisseria cinerea* Cas9 (NcCas9). In further embodiments, the CRISPR/Cas nuclease can be *Francisella novicida* Cpf1 (FnCpf1), *Acidaminococcus* sp. Cpf1 (AsCpf1), or *Lachnospiraceae* bacterium ND2006 Cpf1 (LbCpf1).

In general, the CRISPR/Cas nuclease comprises a RNA recognition and/or RNA binding domain, which interacts with the guide RNA. The CRISPR/Cas nuclease also comprises at least one nuclease domain having endonuclease activity. For example, a Cas9 protein comprises a RuvC-like nuclease domain and a HNH-like nuclease domain, and a Cpf1 protein comprises a RuvC-like domain. CRISPR/Cas nucleases can also comprise DNA binding domains, helicase domains, RNase domains, protein-protein interaction domains, dimerization domains, as well as other domains.

The CRISPR/Cas nuclease can further comprise at least one nuclear localization signal, cell-penetrating domain, and/or marker domain. Non-limiting examples of nuclear localization signals include PKKKRKV (SEQ ID NO:1), PKKKRRV (SEQ ID NO:2), KRPAATKKAGQAKKKK (SEQ ID NO:3), YGRKKRRQRRR (SEQ ID NO:28, RKKRRQRRR (SEQ ID NO:29), PAAKRVKLD (SEQ ID NO:30), RQRRNELKRSP (SEQ ID NO:31), VSRKRPRP (SEQ ID NO:32), PPKKARED (SEQ ID NO:33), PQPKKKPL (SEQ ID NO:34), SALIKKKKKMAP (SEQ ID NO:35), PKQKKRK (SEQ ID NO:36), RKLKKKIKKL (SEQ ID NO:37), REKKKFLKRR (SEQ ID NO:38), KRKGDEVDGVDEVAKKKSKK (SEQ ID NO:39), RKCLQAGMNLEARKTKK (SEQ ID NO:40), NQSSNFGPMKGGNFGGRSSGPYGGGGQYFAKPRNQGGY (SEQ ID NO:41), and RMRIZFKNKGKDTAELRRRRVEVSVELRKAKKDEQILKRRNV (SEQ ID NO:42). Examples of suitable cell-penetrating domains include, without limit, GRKKRRQRRRPPQPKKKRKV (SEQ ID NO:4), PLSSIFSRIGDPPKKKRKV (SEQ ID NO:5), GALFLGWLGAAGSTMGAPKKKRKV (SEQ ID NO:6), GALFLGFLGAAGSTMGAWSQPKKKRKV (SEQ ID NO: 7), KETWWETWWTEWSQPKKKRKV (SEQ ID NO: 8), YARAAARQARA (SEQ ID NO:43), THRLPRRRRRR (SEQ ID NO:44), GGRRARRRRRR (SEQ ID NO:45), RRQRRTSKLMKR (SEQ ID NO:46), GWTLNSAGYLLGKINLKALAALAKKIL (SEQ ID NO:47), KALAWEAKLAKALAKALAKHLAKALAKALKCEA (SEQ ID NO:48), and RQIKIWFQNRRMKWKK (SEQ ID NO:49). Marker domains include fluorescent proteins and purification or epitope tags. Suitable fluorescent proteins include, without limit, green fluorescent proteins (e.g., GFP, eGFP, GFP-2, tagGFP, turboGFP, Emerald, Azami Green, Monomeric Azami Green, CopGFP, AceGFP, ZsGreen1), yellow fluorescent proteins (e.g., YFP, EYFP, Citrine, Venus, YPet, PhiYFP, ZsYellow1), blue fluorescent proteins (e.g., BFP, EBFP, EBFP2, Azurite, mKalamal, GFPuv, Sapphire, T-sapphire), cyan fluorescent proteins (e.g., ECFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRasberry, mStrawberry, Jred), and orange fluorescent proteins (e.g., mOrange, mKO, Kusabira-Orange, Monomeric Kusabira-Orange, mTangerine, tdTomato). Non-limiting examples of suitable purification or epitope tags include 6×His, FLAG®, HA, GST, Myc, and the like.

The nuclear localization signal, cell-penetrating domain, and/or marker domain can be located at the N-terminus, the C-terminal, or in an internal location of the protein. In some embodiments, the CRISPR/Cas nuclease can further comprise at least one detectable label. The detectable label can be a fluorophore (e.g., FAM, TMR, Cy3, Cy5, Texas Red, Oregon Green, Alexa Fluors, Halo tags, or suitable fluorescent tag/dye), a chromophore (e.g., biotin, digoxigenin, and the like), quantum dots, or gold particles. The detectable label can be attached via conventional means to any amino acid of the protein.

Guide RNA.

The CRISPR/Cas nuclease system also comprises a guide RNA (gRNA). The guide RNA interacts with the CRISPR/Cas nuclease and the target site to guide the CRISPR/Cas nuclease to the target site in the chromosomal sequence. The target site has no sequence limitation except that the sequence is bordered by a protospacer adjacent motif (PAM). For example, PAM sequences for Cas9 proteins include 3'-NGG, 3'-NGGNG, 3'-NNAGAAW, and 3'-ACAY, and PAM sequences for Cpf1 include 5'-TTN (wherein N is defined as any nucleotide, W is defined as either A or T, and Y is defined an either C or T).

Each guide RNA can comprise three regions: a first region at the 5' end that has complementarity to the target site in the chromosomal DNA sequence, a second region that is internal and forms a stem loop structure, and a third region at the 3' end that remains essentially single-stranded. The second and third regions form a secondary structure that interacts with the CRISPR/Cas protein. The first region of each guide RNA is different (i.e., is sequence specific). The second and third regions can be the same in guide RNAs that complex with a particular CRISPR/Cas protein.

The first region of the guide RNA has complementarity to sequence protospacer sequence) at the target site such that the first region of the guide RNA can base pair with the target sequence. For example, the first region of a SpCas9 guide RNA can comprise $GN_{17-20}GG$. In general, the complementarity between the first region crRNA) of the guide RNA and the target sequence is at least 80%, at least 85%, at least 90%, at least 95%, or more. In various embodiments, the first region of the guide RNA can comprise from about 10 nucleotides to more than about 25 nucleotides. For example, the region of base pairing between the first region of the guide RNA and the target site in the cDNA sequence can be about 10, 11, 12, 13, 14, 15, 16, 17, 18, 19, 20, 22, 23, 24, 25, or more than 25 nucleotides in length. In an exemplary embodiment, the first region of the guide RNA is about 19, 20, or 21 nucleotides in length.

The guide RNA also comprises a second region that forms a secondary structure. In some embodiments, the secondary structure comprises at least one stem (or hairpin) and loop. The length of each loop and the stem can vary. For example, the loop can range from about 3 to about 10 nucleotides in length, and the stem can range from about 6 to about 20 base pairs in length. The stem can comprise one or more bulges of 1 to about 10 nucleotides. Thus, the overall length of the second region can range from about 16 to about 60 nucleotides in length. The guide RNA also comprises a third region at the 3' end that remains essentially single-stranded. Thus, the third region has no complementarity to any nucleic acid sequence in the cell of interest and has no complementarity to the rest of the guide RNA. The length of the third region can vary. In general, the third region is more than about 4 nucleotides in length. For example, the length of the third region can range from about 5 to about 60 nucleotides in length.

The combined length of the second and third regions (also called the universal or scaffold region) of the guide RNA can range from about 30 to about 120 nucleotides in length. In one aspect, the combined length of the second and third regions of the guide RNA range from about 70 to about 100 nucleotides in length.

In still other embodiments, the second and third regions of the guide RNA can comprise one or more additional stem-loop regions, wherein the stem-loop regions comprise aptamer sequences (Konermann et al., Nature 3, 2015, 517(7536):583-588; Zalatan et al., Cell, 2015, 160(1-2):339-50). Suitable aptamer sequences include those that bind adaptor proteins chosen from MS2, PP7, COM, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1, HSF1, AID, APOBEC1, p300, TET1/2/3, VP64, GFP, Rta, p65, MyoD1, or VP160. In such embodiments, the total length of the second and third regions of the guide RNA can range up to about 125 nucleotides, up to about 150 nucleotides, up to about 175 nucleotides, up to about 200 nucleotides, up to about 225 nucleotides, up to about 250 nucleotides, up to about 275 nucleotides, or up to about 300 nucleotides.

In some embodiments, the guide RNA can be a single molecule comprising all three regions. In other embodiments, the guide RNA can comprise two separate molecules. The first RNA molecule (i.e., crRNA) can comprise the first region of the guide RNA and one half of the "stem" of the second region of the guide RNA. The second RNA molecule (i.e., tracrRNA) can comprise the other half of the "stem" of the second region of the guide RNA and the third region of the guide RNA. Thus, in this embodiment, the first and second RNA molecules each contain a sequence of nucleotides that are complementary to one another. For example, in one embodiment, crRNA and tracrRNA RNA molecules each comprise a sequence (of about 6 to about 20 nucleotides) that base pairs with the other sequence to form a functional guide RNA. For example, the guide RNA of type II CRISPR/Cas systems can comprise crRNA and tracrRNA. In some aspects, the crRNA for a type II CRISPR/Cas system can be chemically synthesized and the tracrRNA type II CRISPR/Cas system can be synthesized in vitro (see section (I)(c) below). In other embodiments, the guide RNA of type V CRISPR/Cas systems can comprise only crRNA.

The guide RNA can comprise standard ribonucleotides, modified ribonucleotides (e.g., pseudouridine), ribonucleotide isomers, and/or ribonucleotide analogs. In some embodiments, the guide RNA can further comprise at least one detectable label. The detectable label can be a fluorophore (e.g., FAM, TMR, Cy3, Cy5, Texas Red, Oregon Green, Alexa Fluors, Halo tags, or suitable fluorescent dye), a chromophore (e.g., biotin, digoxigenin, and the like), quantum dots, or gold particles. Those skilled in the art are familiar with gRNA design and construction, e.g., gRNA design tools are available on the internet or from commercial sources.

The guide RNA can be synthesized chemically, synthesized enzymatically, or a combination thereof. For example the guide RNA can be synthesized using standard phosphoramidite-based solid-phase synthesis methods. Alternatively, the guide RNA can be synthesized in vitro by operably linking DNA encoding the guide RNA to a promoter control sequence that is recognized by a phage RNA polymerase. Examples of suitable phage promoter sequences include T7, T3, SP6 promoter sequences, or variations thereof. In embodiments in which the guide RNA comprises two separate molecules (i.e., crRNA and tracrRNA), the crRNA can be chemically synthesized and the tracrRNA can be enzymatically synthesized. The nucleic acid encoding the guide RNA can be part of a plasmid vector, which can further comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. As detailed below in section (I)(c), nucleic acid encoding the guide RNA can be operably linked to a promoter control sequence that is recognized by RNA polymerase III (Pol III) for expression in eukaryotic cells.

(ii) CRISPR/Cas Dual Nickase Systems

In other embodiments, the programmable DNA modification protein can be a CRISPR/Cas dual nickase system. CRISPR/Cas dual nickase systems are similar to the CRISPR/Cas nuclease systems described above in section (I)(a)(i) except that the CRISPR/Cas nuclease is modified to cleave only one strand of DNA. Thus, a single CRISPR/Cas nickase system creates a single-stranded break or a nick in double-stranded DNA, and a paired CRISPR/Cas dual nickase system comprising paired offset guide RNAs creates a double-stranded break in the DNA.

A CRISPR/Cas nuclease can be converted to a nickase by one or more mutations and/or deletions. For example, a Cas9 nickase can comprise one or more mutations in one of the nuclease domains (e.g., the RuvC-like domain or the HNH-like domain). For example, the one or more mutations can be D10A, D8A, E762A, and/or D986A in the RuvC-like domain or the one or more mutations can be H840A, H559A, N854A, N856A, and/or N863A in the HNH-like domain.

(iii) Zinc Finger Nucleases

In still other embodiments, the programmable DNA modification protein can be a zinc finger nuclease (ZFN). A ZFN comprises a DNA binding zinc finger region and a nuclease domain. The zinc finger region can comprise from about two to seven zinc fingers, for example, about four to six zinc fingers, wherein each zinc finger binds three nucleotides. The zinc finger region can be engineered to recognize and bind to any DNA sequence. Zinc finger design tools or algorithms are available on the internet or from commercial sources. The zinc fingers can be linked together using suitable linker sequences.

A ZFN also comprises a nuclease domain, which can be obtained from any endonuclease or exonuclease. Non-limiting examples of endonucleases from which a nuclease domain can be derived include, but are not limited to, restriction endonucleases and homing endonucleases. In some embodiments, the nuclease domain can be derived from a type II-S restriction endonuclease. Type II-S endonucleases cleave DNA at sites that are typically several base pairs away from the recognition/binding site and, as such, have separable binding and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In some embodiments, the nuclease domain can be a FokI nuclease domain or a derivative thereof. The type II-S nuclease domain can be modified to facilitate dimerization of two different nuclease domains. For example, the cleavage domain of FokI can be modified by mutating certain amino acid residues. By way of non-limiting example, amino acid residues at positions 446, 447, 479, 483, 484, 486, 487, 490, 491, 496, 498, 499, 500, 531, 534, 537, and 538 of FokI nuclease domains are targets for modification. For example, one modified FokI domain can comprise Q486E, I499L, and/or N496D mutations, and the other modified FokI domain can comprise E490K, I538K, and/or H537R mutations.

The ZFN can further comprise at least one nuclear localization signal, cell-penetrating domain, and/or marker domain, which are described above in section (I)(a)(i).

(iv) Transcription Activator-like Effector Nucleases

In alternate embodiments, the programmable DNA modification protein can be a transcription activator-like effector nuclease (TALEN). TALENs comprise a DNA binding domain composed of highly conserved repeats derived from transcription activator-like effectors (TALEs) that is linked to a nuclease domain. TALEs are proteins secreted by plant pathogen *Xanthomonas* to alter transcription of genes in host plant cells. TALE repeat arrays can be engineered via modular protein design to target any DNA sequence of interest. The nuclease domain of TALENs can be any nuclease domain as described above in section (I)(a)(iii). In specific embodiments, the nuclease domain is derived from FokI (Sanjana et al., 2012, Nat Protoc, 7(1):171-192).

The TALEN can also comprise at least one nuclear localization signal, cell-penetrating domain, marker domain, and/or detectable label, which are described above in section (I)(a)(i).

(v) Meganucleases or Rare-Cutting Endonucleases

In still other embodiments, the programmable DNA modification protein can be a meganuclease or derivative thereof. Meganucleases are endodeoxyribonucleases characterized by long recognition sequences, i.e., the recognition sequence generally ranges from about 12 base pairs to about 45 base pairs. As a consequence of this requirement, the recognition sequence generally occurs only once in any given genome. Among meganucleases, the family of homing endonucleases named LAGLIDADG has become a valuable tool for the study of genomes and genome engineering. In some embodiments, the meganuclease can be I-SceI, I-TevI, or variants thereof. A meganuclease can be targeted to a specific chromosomal sequence by modifying its recognition sequence using techniques well known to those skilled in the art.

In alternate embodiments, the programmable DNA modification protein can be a rare-cutting endonuclease or derivative thereof. Rare-cutting endonucleases are site-specific endonucleases whose recognition sequence occurs rarely in a genome, preferably only once in a genome. The rare-cutting endonuclease may recognize a 7-nucleotide sequence, an 8-nucleotide sequence, or longer recognition sequence. Non-limiting examples of rare-cutting endonucleases include NotI, AscI, PacI, AsiSI, SbfI, and FseI.

The meganuclease or rare-cutting endonuclease can also comprise at least one nuclear localization signal, cell-penetrating domain, marker domain, and/or detectable label, which are described above in section (I)(a)(i).

(vi) Programmable Fusion Proteins Comprising Nuclease Domains

In yet additional embodiments, the programmable DNA modification protein can be a fusion protein comprising a programmable DNA binding domain linked to a (double-stranded cleavage) nuclease domain. The nuclease domain of the fusion protein can be any of those described above in section (I)(a)(iii), a nuclease domain derived from a CRISPR/Cas nuclease (e.g., RuvC-like or HNH-like nuclease domains of Cas9 or nuclease domain of Cpf1), or a nuclease domain derived from a meganuclease or rare-cutting endonuclease.

The programmable DNA binding domain of the fusion protein can be a programmable endonuclease (i.e., CRISPR/CAS nuclease, or meganuclease) modified to lack all nuclease activity. Thus, the DNA binding domain of the fusion protein can be a catalytically inactive CRISPR/Cas system or a catalytically inactive meganuclease. Alternatively, the programmable DNA binding domain of the fusion protein can be a programmable DNA binding protein such as, e.g., a zinc finger protein or a transcription activator-like effector. In some embodiments, the programmable DNA binding domain can be a catalytically inactive CRISPR/Cas nuclease in which the nuclease activity was eliminated by mutation and/or deletion. For example, the catalytically inactive CRISPR/Cas protein can be a catalytically inactive (dead) Cas9 (dCas9) in which the RuvC-like domain comprises a D10A, D8A, E762A, and/or D986A mutation and the HNH-like domain comprises a H840A, H559A, N854A, N865A, and/or N863A mutation. Alternatively, the catalytically inactive CRISPR/Cas protein can be a catalytically inactive (dead) Cpf1 protein comprising comparable mutations in the nuclease domain. In still other embodiments, the programmable DNA binding domain can be a catalytically inactive meganuclease in which nuclease activity was eliminated by mutation and/or deletion, e.g., the catalytically inactive meganuclease can comprise a C-terminal truncation.

The fusion protein comprising nuclease activity can also comprise at least one nuclear localization signal, cell-penetrating domain, marker domain, and/or detectable label, which are described above in section (I)(a)(i).

(vii) Programmable Fusion Proteins/Complexes Comprising Non-Nuclease Domains

In alternate embodiments, the programmable DNA modification protein can be a fusion protein comprising a programmable DNA binding domain linked to a non-nuclease modification domain. Suitable programmable DNA binding domains are described above in section (I)(a)(vi).

In some embodiments, the non-nuclease modification domain can be an epigenetic modification domain, which alters DNA or chromatin structure (and may or may not alter DNA sequence). Non-limiting examples of suitable epigenetic modification domains include those with DNA methyltransferase activity (e.g., cytosine methyltransferase), DNA demethylase activity, DNA deamination (e.g., cytosine deaminase, adenosine deaminase, guanine deaminase), DNA amination, DNA helicase activity, histone acetyltransferase (HAT) activity (e.g., HAT domain derived from E1A binding protein p300), histone deacetylase activity, histone methyltransferase activity, histone demethylase activity, histone kinase activity, histone phosphatase activity, histone ubiquitin ligase activity, histone deubiquitinating activity, histone adenylation activity, histone deadenylation activity, histone SUMOylating activity, histone deSUMOylating activity, histone ribosylation activity, histone deribosylation activity, histone myristoylation activity, histone demyristoylation activity, histone citrullination activity, histone alkylation activity, histone dealkylation activity, or histone oxidation activity. In specific embodiments, the epigenetic modification domain can comprise cytosine deaminase activity, histone acetyltransferase activity, or DNA methyltransferase activity.

In other embodiments, the non-nuclease modification domain can be a transcriptional activation domain or transcriptional repressor domain. Suitable transcriptional activation domains include, without limit, herpes simplex virus VP16 domain, VP64 (which is a tetrameric derivative of VP16), VP160, NFκB p65 activation domains, p53 activation domains 1 and 2, CREB (cAMP response element binding protein) activation domains, E2A activation domains, activation domain from human heat-shock factor 1 (HSF1), or NFAT (nuclear factor of activated T-cells) activation domains. Non-limiting examples of suitable transcriptional repressor domains include inducible cAMP early repressor (ICER) domains, Kruppel-associated box A (KRAB-A) repressor domains, YY1 glycine rich repressor domains, Sp1-like repressors, E(spl) repressors, IκB repressor, or MeCP2. Transcriptional activation or transcriptional repressor domains can be genetically fused to the DNA binding protein or bound via noncovalent protein-protein, protein-RNA, or protein-DNA interactions.

In embodiments in which the programmable DNA modification protein comprises a CRISPR/Cas system, the guide RNA of the CRISPR/Cas system can comprise aptamer sequences that bind transcriptional activators, transcriptional repressors, or epigenetic modification proteins (Konermann et al., Nature, 2015, 517(7536):583-588; Zalatan et al., Cell, 2015, 160(1-2):339-50).

The fusion protein comprising non-nuclease activity can also comprise at least one nuclear localization signal, cell-penetrating domain, marker domain, and/or detectable label, which are described above in section (I)(a)(i).

(b) Programmable DNA binding Proteins

The composition also comprises at least one programmable DNA binding protein. Programmable DNA binding proteins are proteins that bind to specific DNA sequences but do not modify the DNA or protein(s) associated with DNA.

In some embodiments, the at least one programmable DNA binding protein can be a CRISPR/Cas nuclease modified to lack nuclease activity. For example, the programmable DNA binding protein can be a catalytically inactive CRISPR/Cas system. For this, the CRISPR/Cas nuclease can be modified by mutation and/or deletion to eliminate all nuclease activity. In one embodiment, the RuvC-like domain and the HNH-like domain both comprise one or more mutations and/or deletions to eliminate nuclease activity. For example, the catalytically inactive CRISPR/Cas protein can be a catalytically inactive (dead) Cas9 (dCas9) in which the RuvC-like domain comprises a D10A, D8A, E762A, and/or D986A mutation and the HNH-like domain comprises a H840A, H559A, N854A, N856A, and/or N863A mutation. Alternatively, the catalytically inactive CRISPR/Cas protein can be a catalytically inactive (dead) Cpf1 protein comprising comparable mutations in the nuclease domain. In other aspects, the programmable DNA binding protein can be a CRISPR/Cas protein modified to nick one strand of a double-stranded sequence (i.e., is a nickase), as detailed above in section (I)(a)(ii).

In other embodiments, the at least one programmable DNA binding protein can be a catalytically inactive meganuclease in which nuclease activity was eliminated by mutation and/or deletion, e.g., the catalytically inactive meganuclease can comprise a C-terminal truncation. In still other embodiments, the at least one programmable DNA binding protein can be a zinc finger protein or a transcription activator-like effector (TALE). In additional embodiments, the at least one programmable DNA binding protein can be a CRISPR/Cas nickase, a ZFN nickase, a TALEN nickase, or a meganuclease nickase. ZFN, TALEN, and meganuclease nickases comprise mutations and/or deletions in one of the nuclease domains or half domains, such that the nickase cleave only one strand of a double-stranded sequence.

The programmable DNA binding protein can also comprise at least one nuclear localization signal, cell-penetrating domain, marker domain, and/or detectable label, which are described above in section (I)(a)(i).

(c) Nucleic Acids Encoding Programmable DNA Modification Proteins or Programmable DNA binding Proteins The nucleic acid encoding the programmable DNA modification protein, described above in section (I)(a), or the programmable DNA binding protein, described above in section (I)(b), can be DNA or RNA, linear or circular, single-stranded or double-stranded. The RNA or DNA can be codon optimized for efficient translation into protein in the eukaryotic cell of interest. Codon optimization programs are available as freeware or from commercial sources.

In some embodiments, the nucleic acid encoding the programmable DNA modification protein or the at least one programmable DNA binding protein can be mRNA. The mRNA can be synthesized in vitro. For this, DNA encoding the DNA modification protein or the at least one DNA binding protein can be operably linked to a promoter sequence that is recognized by a phage RNA polymerase for in vitro synthesis of mRNA. For example, the promoter sequence can be a T7, T3, or SP6 promoter sequence or a variation of a T7, T3, or SP6 promoter sequence. In such embodiments, the in vitro-transcribed RNA can be purified, capped, and/or polyadenylated. As detailed below, the DNA encoding the DNA modification protein or the DNA binding protein can be part of a vector.

In other embodiments, the nucleic acid encoding the programmable DNA modification protein or the at least one programmable DNA binding protein can be DNA. The DNA sequence encoding the programmable DNA modification protein or the at least one programmable DNA binding protein can be operably linked to at least one promoter control sequence for expression in the cell of interest. In some embodiments, the DNA coding sequence also can be linked to a polyadenylation signal (e.g., SV40 polyA signal, bovine growth hormone (BGH) polyA signal, etc.) and/or at least one transcriptional termination sequence.

In certain embodiments, the DNA coding sequence can be operably linked to a promoter sequence for expression of the DNA modification protein or the DNA binding protein in bacterial (e.g., E. coli) cells or eukaryotic (e.g., yeast, insect, or mammalian) cells. Suitable bacterial promoters include, without limit, T7 promoters, lac operon promoters, trp promoters, tac promoters (which are hybrids of trp and lac promoters), variations of any of the foregoing, and combinations of any of the foregoing. Non-limiting examples of suitable eukaryotic promoters include constitutive, regulated, or cell- or tissue-specific promoters. Suitable eukaryotic constitutive promoter control sequences include, but are not limited to, cytomegalovirus immediate early promoter (CMV), simian virus (SV40) promoter, adenovirus major late promoter, Rous sarcoma virus (RSV) promoter, mouse mammary tumor virus (MMTV) promoter, phosphoglycerate kinase (PGK) promoter, elongation factor (ED1)-alpha promoter, ubiquitin promoters, actin promoters, tubulin promoters, immunoglobulin promoters, fragments thereof, or combinations of any of the foregoing. Examples of suitable eukaryotic regulated promoter control sequences include without limit those regulated by heat shock, metals, steroids, antibiotics, or alcohol. Non-limiting examples of tissue-specific promoters include B29 promoter, CD14 promoter, CD43 promoter, CD45 promoter, CD68 promoter, desmin promoter, elastase-1 promoter, endoglin promoter, fibronectin promoter, Flt-1 promoter, GFAP promoter, GPIIb promoter, ICAM-2 promoter, INF-β promoter, Mb promoter, NphsI promoter, OG-2 promoter, SP-B promoter, SYN1 promoter, and WASP promoter. The promoter sequence can be wild type or it can be modified for more efficient or efficacious expression.

In various embodiments, nucleic acid encoding the programmable DNA modification protein and/or the at least one programmable DNA binding protein can be present in a vector. Suitable vectors include plasmid vectors, phagemids, cosmids, artificial/mini-chromosomes, transposons, and viral vectors (e.g., lentiviral vectors, adeno-associated viral vectors, adenoviral vectors, etc.). In one embodiment, the DNA encoding the programmable DNA modification protein and/or the at least one programmable DNA binding protein can be present in a plasmid vector. Non-limiting examples of suitable plasmid vectors include pUC, pBR322, pET, pBluescript, and variants thereof. In other embodiments, nucleic acid encoding the programmable DNA modification protein and/or the at least one programmable DNA binding protein can be present in a viral vector. The plasmid or viral vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., $3^{rd}$ edition, 2001.

In embodiments in which the programmable DNA modification protein and/or the at least one programmable DNA binding protein comprises a CRISPR/Cas protein or variant thereof, the expression vector comprising nucleic acid encoding the programmable DNA modification protein and/or the at least one programmable DNA binding protein can further comprise sequence encoding one or more guide RNAs. The sequence encoding the guide RNA generally is operably linked to at least one transcriptional control sequence for expression of the guide RNA in the eukaryotic cell of interest. For example, nucleic acid encoding the guide RNA can be operably linked to a promoter sequence that is recognized by RNA polymerase III (Pol III). Examples of suitable Pol III promoters include, but are not limited to, mammalian U6, U3, H1, and 7SL RNA promoters.

(d) Specific Compositions

In some embodiments, the programmable DNA modification protein and the one or more programmable DNA binding proteins are provided as proteins (or, in some instances, as protein-RNA complexes). The programmable DNA modification proteins and the programmable DNA binding proteins can be expressed in bacterial or eukaryotic cells and purified using means well known in the art. In other embodiments, the programmable DNA modification protein and the one or more programmable DNA binding protein are provided as encoding nucleic acids.

In some embodiments, the composition can comprise one programmable DNA binding protein/system or encoding nucleic acids. In other embodiments, the composition can comprise two programmable DNA binding proteins/systems or encoding nucleic acids. In yet other embodiments, the composition can comprise three programmable DNA binding proteins/systems or encoding nucleic acids. In further embodiments, the composition can comprise four programmable DNA binding proteins/systems or encoding nucleic acids. In still other embodiments, the composition can comprise five or more programmable DNA binding proteins/system or encoding nucleic acids.

In specific embodiments, the programmable DNA modification protein can comprise a CRISPR/Cas system (e.g., CRISPR/Cas nuclease, CRISPR/Cas dual nickase, or catalytically inactive (dead) CRISPR/Cas protein linked to a non-nuclease modification domain) and the programmable DNA binding protein can be a CRISPR/Cas system that lacks nuclease activity. For example, the programmable DNA binding protein can be a catalytically inactive CRISPR/Cas system. In general, each CRISPR/Cas protein comprises at least one nuclear localization signal. In some iterations, the composition can comprise the CRISPR/Cas systems as CRISPR/Cas proteins and guide RNA, wherein the protein and RNA can be separate entities or the protein and RNA can be complexed together. The guide RNA can be at least partially chemically synthesized. The guide RNA can be enzymatically synthesized. In other iterations, the composition can comprise the CRISPR/Cas proteins and DNA encoding the guide RNAs. In still other iterations, the composition can comprise mRNA encoding the CRISPR/Cas proteins and DNA encoding the guide RNAs. In yet other iterations, the composition can comprise plasmid or viral vectors encoding the CRISPR/Cas proteins and/or the guide RNAs. In certain embodiments, the catalytically active CRISPR/Cas protein and the catalytically inactive (dead) CRISPR/Cas protein are Cas9 proteins. Nucleic acids encoding the CRISPR/Cas proteins are generally codon optimized for optimal expression in the eukaryotic cell of interest.

(II) Kits

A further aspect of the present disclosure provides kits comprising the compositions detailed above in section (I). The kits can provide the programmable DNA modification protein and the at least one programmable DNA binding proteins as proteins, as protein-RNA complexes, or as nucleic acids encoding the various components, as detailed above. The kits can further comprise transfection reagents, cell growth media, selection media, in-vitro transcription reagents, nucleic acid purification reagents, protein purification reagents, buffers, and the like. The kits provided herein generally include instructions for carrying out the methods detailed below. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

In some embodiments, the programmable DNA modification protein and/or the at least one programmable DNA binding protein of the kit can comprise a type II CRISPR/Cas system. In certain embodiments, the guide RNA of the type II CRISPR/Cas system can comprise crRNA and tracrRNA. The kit, therefore, can provide the universal tracrRNA(s), and the end user of kit can provide the sequence-specific crRNA(s). In some aspects, the kit can comprise the type II CRISPR/Cas protein(s) and the tracrRNA(s). In other aspects, the kit can comprise mRNA or DNA encoding the type II CRISPR/Cas protein(s) and DNA encoding the tracrRNA(s).

In still other embodiments, the programmable DNA modification protein and/or the at least one programmable DNA binding protein of the kit can comprise a type V CRISPR/Cas system. As detailed above, the guide RNA of type V CRISPR/Cas systems comprises only crRNA. In some aspects, the kit can comprise the type V CRISPR/Cas protein(s) and crRNA(s), or the kit can comprise mRNA or DNA encoding the type V CRISPR/Cas protein(s) and DNA encoding the crRNA(s), In other aspects, the kit can comprise only the type V CRISPR/Cas protein(s) or nucleic acid encoding the type V CRISPR/Cas protein(s), wherein the end user of the kit provides the crRNA(s).

(III) Methods for Increasing Accessibility to Targeted Chromosomal Sites

Another aspect of the present disclosure encompasses methods for increasing the efficiency and/or specificity of targeted genome/epigenetic modification in eukaryotic cells by increasing the accessibility of a programmable DNA modification protein to its target sequence in chromosomal DNA. The methods comprise introducing into the eukaryotic cell of interest (a) a programmable DNA modification protein or nucleic acid encoding the programmable DNA modification protein and (a) at least one programmable DNA binding protein or nucleic acid encoding the at least one programmable DNA binding protein. The programmable DNA modification protein is engineered to recognize and bind to a target sequence in chromosomal DNA, at which site the DNA modification protein can modify the DNA or associated protein(s). Each of the one or more programmable DNA binding protein is engineered to recognize and bind a sequence proximal to the target chromosomal sequence of the DNA modification protein. The programmable DNA modification proteins and programmable DNA binding proteins are detailed above in section (I).

In general, the sequence proximal to the target chromosomal sequence is located within about 250 base pairs on either side (i.e., upstream or downstream) of the target chromosomal sequence. The proximal site(s) can be located on either strand of the duplex DNA. In some embodiments, the sequence proximal to the target chromosomal sequence can be located less than about 250 bp, less than about 200 bp, less than about 150 bp, less than about 100 bp, less than about 75 bp, less than about 50 bp, less than about 25 bp, less than about 20 bp, less than about 15 bp, less than about 10 bp, or less than about 5 bp from the target chromosomal sequence of the DNA modification protein. In certain embodiments, the sequence proximal to the target chromosomal sequence can be located from about 1 bp to about 10 bp, from about 11 bp to about 20 bp, from about 21 bp to about 30 bp, from about 31 bp to about 40 bp, from about 41 bp to about 50 bp, from about 51 bp to about 60 bp, from about 61 bp to about 70 bp, from about 71 bp to about 80 bp, from about 81 bp to about 90 bp, from about 91 bp to about 100 bp, from about 101 bp to about 150 bp, from about 151 bp to about 200 bp, or from about 201 bp to about 250 bp on either side of the target chromosomal sequence. In other embodiments, the sequence proximal to the target chromosomal sequence can be located from about 5 bp to about 75 bp, from about 10 bp to about 50 bp, or from about 15 bp to about 25 bp on either side of the target chromosomal sequence.

In some embodiments, the method comprises introducing into the cell at least one programmable DNA binding protein whose binding sequence is located either upstream or downstream of the target chromosomal sequence. In other embodiments, the method comprises introducing into the cell at least two programmable DNA binding proteins, wherein the binding sequence of one is located upstream of the target chromosomal sequence and the binding sequence of the other is located downstream of the target chromosomal sequence. In further embodiments, the method comprises introducing into the cell at least three programmable DNA binding proteins whose binding sequences are located either upstream or downstream of the target chromosomal sequence. In additional embodiments, the method comprises introducing into the cell four or more programmable DNA binding proteins whose binding sequences are located either upstream or downstream of the target chromosomal sequence. In these embodiments, for example, the method may comprise introducing one, two three, four, five, six, seven, eight, nine, ten, or more than ten programmable DNA binding proteins whose binding sequences are located within about 250 bp on either side (i.e., upstream or downstream) of the target chromosomal sequence.

The binding of each of the one or more programmable DNA binding proteins to the site proximal to the target chromosomal sequence changes local chromatin configuration, leading to increased accessibility of the programmable DNA modification protein to the (previously inaccessible) target chromosomal sequence (see FIG. 1). As a consequence, the efficiency of modification by the DNA modification protein is increased (see, e.g., Examples 1-3). Stated another way, the efficiency of modification by a DNA modification protein is increased when the DNA modification protein is introduced into the cell in combination with one or more programmable DNA binding proteins as compared to when the DNA modification protein is introduced into the cell alone.

Moreover, the methods disclosed herein increase the specificity of targeted genome modification. Although the programmable DNA modification protein is engineered to recognize and bind a target sequence in a specific chromosomal locus, identical or near identical sequences can exist in other chromosomal locations (resulting in off-target effects). In embodiments in which the binding of a programmable DNA modification protein to a target chromosomal sequence largely depends on the binding of one or more programmable DNA binding proteins to sequences proximal to the target chromosomal sequence, the binding of the one or more programmable DNA binding proteins to site(s) proximal to the target sequence in the chromosomal locus of interest, however, provides additional specificity to the modification event (see Example 4).

Thus, the methods disclosed herein can increase the efficiency and/or specificity of targeted genome editing (e.g., gene corrections, gene knock-outs, gene knock-ins, and the like), targeted epigenetic modifications, and targeted transcriptional regulation.

(a) Introduction into the Cell

As described, the method comprises introducing into the cell (a) a programmable DNA modification protein or nucleic acid encoding the programmable DNA modification protein and (b) at least one programmable DNA binding protein or nucleic acid encoding the at least one programmable DNA binding protein. Programmable DNA modification proteins are detailed above in section (I)(a), programmable DNA binding proteins are detailed above in section (I)(b), and nucleic acids encoding the DNA modification proteins or the programmable DNA binding protein are described above in section (I)(c).

The programmable DNA modification protein or nucleic acid encoding the programmable DNA modification protein and the at least one programmable DNA binding protein or nucleic acid encoding the at least one programmable DNA binding protein can be introduced into the cell of interest by a variety of means.

In some embodiments, the cell can be transfected with the appropriate molecules (i.e., protein, DNA, and/or RNA). Suitable transfection methods include nucleofection (or electroporation), calcium phosphate-mediated transfection, cationic polymer transfection (e.g., DEAE-dextran or polyethylenimine), viral transduction, virosome transfection, virion transfection, liposome transfection, cationic liposome transfection, immunoliposome transfection, nonliposomal lipid transfection, dendrimer transfection, heat shock transfection, magnetofection, lipofection, gene gun delivery, impalefection, sonoporation, optical transfection, and proprietary agent-enhanced uptake of nucleic acids. Transfection methods are well known in the art (see, e.g., "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001). In other embodiments, the molecules can be introduced into the cell by microinjection. For example, the molecules can be injected into the cytoplasm or nuclei of the cells of interest. The amount of each molecule introduced into the cell can vary, but those skilled in the art are familiar with means for determining the appropriate amount.

The various molecules can be introduced into the cell simultaneously or sequentially. For example, the programmable DNA modification protein (or its encoding nucleic acid) and the at least one programmable DNA binding protein (or encoding nucleic acid) can be introduced at the same time. Alternatively, one can be introduced first and then the other can be introduced later into the cell.

In general, the cell is maintained under conditions appropriate for cell growth and/or maintenance. Suitable cell culture conditions are well known in the art and are described, for example, in Santiago et al., Proc. Natl. Acad. Sci. USA, 2008, 105:5809-5814; Moehle et al. Proc. Natl. Acad. Sci. USA, 2007, 104:3055-3060; Urnov et al., Nature, 2005, 435:646-651; and Lombardo et al., Nat. Biotechnol., 2007, 25:1298-1306. Those of skill in the art appreciate that methods for culturing cells are known in the art and can and will vary depending on the cell type. Routine optimization may be used, in all cases, to determine the best techniques for a particular cell type.

(b) Targeted Genome Modification

The binding of the one or more programmable DNA binding proteins to sequence(s) proximal to the target chromosomal sequence changes local chromatin configuration, e.g., nucleosomal structure can be altered and/or histones can be displaced. As a consequence, the programmable DNA modification protein is able to better access the target chromosomal sequence as compared to when the programmable DNA modification protein is used alone. The increased accessibility results in increased efficiency and/or specificity of targeted genome modification. The targeted genome/epigenetic modification can be mediated by DNA modification proteins having nuclease activity or non-nuclease activity.

In embodiments in which the programmable DNA modification protein has nuclease activity, the DNA modification protein can introduce a double-stranded break at the targeted chromosomal sequence. The double-stranded break in the chromosomal sequence can be repaired by a non-homologous end-joining (NHEJ) repair process. Because NHEJ is error-prone, deletions of at least one nucleotide, insertions of at least one nucleotide, substitutions of at least one nucleotide, or combinations thereof can occur during the repair of the break. Accordingly, the targeted chromosomal sequence can be modified or inactivated. For example, a deletion, insertion, or substitution in the shift in the reading frame of a coding sequence can lead to an altered protein product, or no protein product (which is termed a "knock out"). In some iterations, the method can further comprise introducing into the cell a donor polynucleotide (see below) comprising a donor sequence that is flanked by sequence having substantial sequence identity to sequences located on either side of the target chromosomal sequence, such that during repair of the double-stranded break by a homology directed repair process (HDR) the donor sequence in the donor polynucleotide can be exchanged with or integrated into the chromosomal sequence at the target chromosomal sequence. Integration of an exogenous sequence is termed a "knock in." As detailed above, the methods disclosed herein also reduce off-target effects, thereby increasing the specificity of the targeted genome modification.

In various iterations, therefore, the efficiency and/or specificity of targeted genome modification can be increased by at least about 0.1-fold, at least about 0.5-fold, at least about 1-fold, at least about 2-fold, at least about 5-fold, at least about 10-fold, or at least about 20-fold, at least about 50-fold, at least about 100-fold, or more than about 100-fold relative to when the programmable DNA modification protein having nuclease activity is used alone. For example, the programmable DNA modification protein having nuclease activity, when used alone, can have no detectable indels or integration events. However, when the programmable DNA modification protein having nuclease activity is used in combination with at least one programmable DNA binding protein, indels and integration events can be detected (e.g., at least about 1% indels/integrations, at least about 5% indels/integration, at least about 10% indels/integrations, at least about 20% indels/integrations, at least about 30% indels/integrations, at least about 40% indels/integrations, at least about 50% indels/integrations, or more than about 50% indels/integrations).

In embodiments in which the programmable DNA modification protein has non-nuclease activity, the DNA modification protein can modify DNA or associated proteins at the target chromosomal sequence or modify expression of the target chromosomal sequence. For example, when the programmable DNA modification protein comprises epigenetic modification activity, the status of histone acetylation, methylation, phosphorylation, adenylation, etc. can be modified or the status of DNA methylation, amination, etc. can be modified. As an example, in embodiments in which the programmable DNA modification protein comprises cytosine deaminase activity, one or more cytosine residues at the target chromosomal sequence can be converted to uracil residues. Alternatively, when the programmable DNA modification protein comprises transcriptional activation or repressor activity, transcription at target chromosomal sequence can be increased or decreased. The resultant epigenetic modification or transcriptional regulation can be increased by at least about 0.1-fold, at least about 0.5-fold, at least about 1-fold, at least about 2-fold, at least about 5-fold, at least about 10-fold, or at least about 20-fold, at least about 50-fold, at least about 100-fold, or more than about 100-fold relative to when the programmable DNA modification protein having non-nuclease activity is used alone.

The targeted genome modifications/epigenetic modifications detailed above can be performed singly or multiplexed (i.e., two or more chromosomal sequences can be targeted simultaneously).

(c) Optional Donor Polynucleotide

In embodiments in which the programmable DNA modification protein comprises nuclease activity, the method can further comprise introducing at least one donor polynucleotide into the cell. The donor polynucleotide can be single-stranded or double-stranded, linear or circular, and/or RNA or DNA. In some embodiments, the donor polynucleotide can be a vector, e.g., a plasmid vector.

The donor polynucleotide comprises at least one donor sequence. In some aspects, the donor sequence of the donor polynucleotide can be a modified version of an endogenous or native chromosomal sequence. For example, the donor sequence can be essentially identical to a portion of the chromosomal sequence at or near the sequence targeted by the DNA modification protein, but which comprises at least one nucleotide change. Thus, upon integration or exchange with the native sequence, the sequence at the targeted chromosomal location comprises at least one nucleotide change. For example, the change can be an insertion of one or more nucleotides, a deletion of one or more nucleotides, a substitution of one or more nucleotides, or combinations thereof. As a consequence of the "gene correction" integration of the modified sequence, the cell can produce a modified gene product from the targeted chromosomal sequence.

In other aspects, the donor sequence of the donor polynucleotide can be an exogenous sequence. As used herein, an "exogenous" sequence refers to a sequence that is not native to the cell, or a sequence whose native location is in a different location in the genome of the cell. For example, the exogenous sequence can comprise protein coding sequence, which can be operably linked to an exogenous promoter control sequence such that, upon integration into the genome, the cell is able to express the protein coded by the integrated sequence. Alternatively, the exogenous sequence can be integrated into the chromosomal sequence such that its expression is regulated by an endogenous promoter control sequence. In other iterations, the exogenous sequence can be a transcriptional control sequence, another expression control sequence, an RNA coding sequence, and so forth. As noted above, integration of an exogenous sequence into a chromosomal sequence is termed a "knock in."

As can be appreciated by those skilled in the art, the length of the donor sequence can and will vary. For example, the donor sequence can vary in length from several nucleotides to hundreds of nucleotides to hundreds of thousands of nucleotides.

Typically, the donor sequence in the donor polynucleotide is flanked by an upstream sequence and a downstream sequence, which have substantial sequence identity to sequences located upstream and downstream, respectively, of the sequence targeted by the programmable DNA modification protein. Because of these sequence similarities, the upstream and downstream sequences of the donor polynucleotide permit homologous recombination between the donor polynucleotide and the targeted chromosomal sequence such that the donor sequence can be integrated into (or exchanged with) the chromosomal sequence.

The upstream sequence, as used herein, refers to a nucleic acid sequence that shares substantial sequence identity with a chromosomal sequence upstream of the sequence targeted by the programmable DNA modification protein. Similarly, the downstream sequence refers to a nucleic acid sequence that shares substantial sequence identity with a chromosomal sequence downstream of the sequence targeted by the programmable DNA modification protein. As used herein, the phrase "substantial sequence identity" refers to sequences having at least about 75% sequence identity. Thus, the upstream and downstream sequences in the donor polynucleotide can have about 75%, 76%, 77%, 78%, 79%, 80%, 81%, 82%, 83%' 84%, 85%, 86%, 87%, 88%, 89%, 90%, 91%, 92%, 93%, 94%, 95%, 96%, 97%, 98%, or 99% sequence identity with sequence upstream or downstream to the target sequence. In an exemplary embodiment, the upstream and downstream sequences in the donor polynucleotide can have about 95% or 100% sequence identity with chromosomal sequences upstream or downstream to the sequence targeted by the programmable DNA modification protein.

In some embodiments, the upstream sequence shares substantial sequence identity with a chromosomal sequence located immediately upstream of the sequence targeted by the programmable DNA modification protein. In other embodiments, the upstream sequence shares substantial sequence identity with a chromosomal sequence that is located within about one hundred (100) nucleotides upstream from the target sequence. Thus, for example, the upstream sequence can share substantial sequence identity with a chromosomal sequence that is located about 1 to about 20, about 21 to about 40, about 41 to about 60, about 61 to about 80, or about 81 to about 100 nucleotides upstream from the target sequence. In some embodiments, the downstream sequence shares substantial sequence identity with a chromosomal sequence located immediately downstream of the sequence targeted by the programmable DNA modification protein. In other embodiments, the downstream sequence shares substantial sequence identity with a chromosomal sequence that is located within about one hundred (100) nucleotides downstream from the target sequence. Thus, for example, the downstream sequence can share substantial sequence identity with a chromosomal sequence that is located about 1 to about 20, about 21 to about 40, about 41 to about 60, about 61 to about 80, or about 81 to about 100 nucleotides downstream from the target sequence.

Each upstream or downstream sequence can range in length from about 20 nucleotides to about 5000 nucleotides. In some embodiments, upstream and downstream sequences can comprise about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2800, 3000, 3200, 3400, 3600, 3800, 4000, 4200, 4400, 4600, 4800, or 5000 nucleotides. In specific embodiments, upstream and downstream sequences can range in length from about 50 to about 1500 nucleotides.

(e) Cell Types

A variety of cells are suitable for use in the methods disclosed herein. In general, the cell is a eukaryotic cell. For example, the cell can be a human mammalian cell, a non-human mammalian cell, a non-mammalian vertebrate cell, an invertebrate cell, an insect cell, a plant cell, a yeast cell, or a single cell eukaryotic organism. In some embodiments, the cell can also be a one cell embryo. For example, a non-human mammalian embryo including rat, hamster, rodent, rabbit, feline, canine, ovine, porcine, bovine, equine, and primate embryos. In still other embodiments, the cell can be a stem cell such as embryonic stem cells, ES-like stem cells, fetal stem cells, adult stem cells, and the like. In one embodiment, the stem cell is not a human embryonic stem cell. Furthermore, the stem cells may include those made by the techniques disclosed in WO2003/046141, which is incorporated herein in its entirety, or Chung et al. (Cell Stem Cell, 2008, 2:113-117). The cell can be in vitro or in vivo (i.e., within an organism). In exemplary embodiments, the cell is a mammalian cell. In particular embodiments, the cell is a human cell.

Non-limiting examples of suitable mammalian cells include human embryonic kidney cells (HEK293, HEK293T); human cervical carcinoma cells (HELA); human lung cells (W138); human liver cells (Hep G2); human U2-OS osteosarcoma cells, human A549 cells, human A-431 cells, and human K562 cells; Chinese hamster ovary (CHO) cells, baby hamster kidney (BHK) cells; mouse myeloma NS0 cells, mouse embryonic fibroblast 3T3 cells (NIH3T3), mouse B lymphoma A20 cells; mouse melanoma B16 cells; mouse myoblast C2C12 cells; mouse myeloma SP2/0 cells; mouse embryonic mesenchymal C3H-10T1/2 cells; mouse carcinoma CT26 cells, mouse prostate DuCuP cells; mouse breast EMT6 cells; mouse hepatoma Hepa1c1c7 cells; mouse myeloma J5582 cells; mouse epithelial MTD-1A cells; mouse myocardial MyEnd cells; mouse renal RenCa cells; mouse pancreatic RIN-5F cells; mouse melanoma X64 cells; mouse lymphoma YAC-1 cells; rat glioblastoma 9L cells; rat B lymphoma RBL cells; rat neuroblastoma B35 cells; rat hepatoma cells (HTC); buffalo rat liver BRL 3A cells; canine kidney cells (MDCK); canine mammary (CMT) cells; rat osteosarcoma D17 cells; rat monocyte/macrophage DH82 cells; monkey kidney SV-40 transformed fibroblast (COS 7) cells; monkey kidney CVI-76 cells; African green monkey kidney (VERO-76) cells. An extensive list of mammalian cell lines may be found in the American Type Culture Collection catalog (ATCC, Manassas, Va.).

(IV) Methods for Detecting Specific Genomic Loci

Also provided herein are methods for detecting or visualizing specific genomic loci in eukaryotic cells. Since the proximal binding of the one or more programmable DNA binding protein(s) alters chromatin structure and increases access of the programmable DNA modification protein to previously inaccessible chromosomal loci, the method described above in section (III) can be modified to enhance detection of specific genomic loci or targeted chromosomal sequences. The method comprises introducing into the eukaryotic cell (a) a programmable DNA binding protein comprising at least one detectable marker domain or nucleic acid encoding the programmable DNA binding protein comprising at least one detectable marker domain, and (b) at least one programmable DNA binding protein or nucleic acid encoding the at least one programmable DNA binding protein, wherein the programmable DNA binding protein comprising at least one detectable marker domain is targeted to a target chromosomal sequence and each of the one or more programmable DNA binding proteins is targeted to a site proximal to the target chromosomal sequence. Binding of the at least one programmable DNA binding protein to the site proximal to the target chromosomal sequence increases accessibility of the programmable DNA binding protein comprising at least one detectable marker domain to the target chromosomal sequence. The method further comprises detecting the programmable DNA binding protein comprising at least one detectable marker domain bound to the target chromosomal sequence.

The programmable DNA binding protein comprising at least one detectable marker domain comprises a programmable DNA binding domain. Suitable programmable DNA binding domains are described above in section (I)(a)(vi). In specific embodiments, the programmable DNA binding domain can be a catalytically inactive CRISPR/Cas system, a catalytically inactive meganuclease, a zinc finger protein, or a transcription activator-like effector. The at least one detectable marker domain of the programmable DNA binding protein can be a fluorescent protein (e.g., GFP. eGFP, RFP, and the like), a fluorescent tag, or an epitope tag (which are described in section (I)(a)(i) above). In certain embodiments, the at least one detectable marker domain of the programmable DNA binding protein can be a naturally occurring epitope within the programmable DNA binding protein, such that the programmable DNA binding protein can be detected by an antibody against the programmable DNA binding protein. The programmable DNA binding protein comprising at least one detectable marker domain can further comprise at least one nuclear localization signal and/or cell-penetrating domain, as described above in section (I)(a)(i). In some embodiments, the programmable DNA binding protein comprising at least one detectable marker domain can further comprise a non-nuclease modification domain (as described above in section (I)(a)(vi) above).

The one or more programmable DNA binding proteins are described above in section (I)(b). In general, the at least one programmable DNA binding can be a catalytically inactive CRISPR/Cas protein, a catalytically inactive meganuclease, a zinc finger protein, a transcription activator-like effector, a CRISPR/Cas nickase, a ZFN nickase, a TALEN nickase, or a meganuclease nickase.

The method further comprises detecting the programmable DNA binding protein comprising the detectable marker domain that is bound to the target chromosomal sequence, wherein the detecting can be via dynamic live cell imaging, fluorescent microscopy, confocal microscopy, immunofluorescence, immunodetection, RNA-protein binding, protein-protein binding, and the like. The detecting step can be performed in live cells or fixed cells.

In embodiments in which the method comprises detecting chromatin structural dynamics in live cells, the programmable DNA binding protein comprising the detectable marker domain and the one or more programmable DNA binding proteins can be introduced into the cell as proteins or nucleic acids, essentially as described above in section (III)(a). In embodiments in which the method comprises detecting the targeted chromosomal sequence in fixed cells, the programmable DNA binding protein comprising the detectable marker domain and the programmable DNA binding proteins can be introduced into the cell as proteins (or RNA-protein complexes). Means for fixing and permeabilizing cells are well known in the art. In some embodiments, the fixed cells can be subjected to chemical and/or thermal denaturation processes to convert double-stranded chromosomal DNA into single-stranded DNA. In other embodiments, the fixed cells are not subjected to chemical and/or thermal denaturation processes.

In specific embodiments, the programmable DNA binding protein comprising the detectable marker domain is a fusion protein comprising a catalytically inactive (or dead) CRISPR/Cas protein and a fluorescent protein marker domain, and the at least one programmable DNA binding protein is a catalytically inactive (or dead) CRISPR/Cas protein.

In embodiments in which at least one of the programmable DNA modification or DNA binding proteins comprises a CRISPR/Cas protein, the guide RNA can further comprise a detectable label for in situ detection (e.g., FISH or CISH). Detectable labels are detailed above in section (I)(a)(i). In some embodiments, each of the programmable DNA modification and DNA binding proteins comprises a CRISPR/Cas protein and each guide RNA comprises at least one detectable label, thereby increasing the amount or intensity of the signal to be detected.

In still other embodiments, the proximally bound programmable DNA modification protein and the one or more programmable DNA binding proteins can be detected via a proximal ligation assay. For example, the programmable DNA modification protein can be bound by a first antibody and at least one of the programmable DNA binding proteins can be bound by a second antibody, each of which is linked, directly or indirectly (e.g., via secondary antibodies), to a single-stranded proximity detection oligonucleotide. In other embodiments, single-stranded proximity detection oligonucleotide(s) can be linked, directly or indirectly, to guide RNA(s). In yet other embodiments, single-stranded proximity detection oligonucleotide(s) can be linked, directly or indirectly, to the programmable DNA modification or programmable DNA binding proteins. The proximity detection oligonucleotides, which are complexed with the proximally located, chromosomally-bound proteins, can be detected via an in situ proximity-dependent amplification reaction. The in situ proximity-dependent amplification reaction can be a proximity ligation assay (PLA, see Söderberg, et al., Nature Methods, 2006, 3(12):995-1000) or a proximity-dependent initiation of hybridization chain reaction (proxHCR, see Koos et al., Nature Communications, 2015, 6:7294, 10 pp.).

(V) Applications

The compositions and methods disclosed herein can be used in a variety of therapeutic, diagnostic, industrial, and research applications. In some embodiments, the present disclosure can be used to modify any chromosomal sequence of interest in a cell, animal, or plant in order to model and/or study the function of genes, study genetic or epigenetic conditions of interest, or study biochemical pathways involved in various diseases or disorders. For example, transgenic organisms can be created that model diseases or disorders, wherein the expression of one or more nucleic acid sequences associated with a disease or disorder is altered. The disease model can be used to study the effects of mutations on the organism, study the development and/or progression of the disease, study the effect of a pharmaceutically active compound on the disease, and/or assess the efficacy of a potential gene therapy strategy.

In other embodiments, the compositions and methods can be used to perform efficient and cost effective functional genomic screens, which can be used to study the function of genes involved in a particular biological process and how any alteration in gene expression can affect the biological process, or to perform saturating or deep scanning mutagenesis of genomic loci in conjunction with a cellular phenotype. Saturating or deep scanning mutagenesis can be used to determine critical minimal features and discrete vulnerabilities of functional elements required for gene expression, drug resistance, and reversal of disease, for example.

In further embodiments, the compositions and methods disclosed herein can be used for diagnostic tests to establish the presence of a disease or disorder and/or for use in determining treatment options. Examples of suitable diagnostic tests include detection of specific mutations in cancer cells (e.g., specific mutation in EGFR, HER2, and the like), detection of specific mutations associated with particular diseases (e.g., trinucleotide repeats, mutations in β-globin associated with sickle cell disease, specific SNPs, etc.), detection of hepatitis, detection of viruses (e.g., Zika), and so forth.

In additional embodiments, the compositions and methods disclosed herein can be used to correct genetic mutations associated with a particular disease or disorder such as, e.g., correct globin gene mutations associated with sickle cell disease or thalassemia, correct mutations in the adenosine deaminase gene associated with severe combined immune deficiency (SCID), reduce the expression of HTT, the disease-causing gene of Huntington's disease, or correct mutations in the rhodopsin gene for the treatment of retinitis pigmentosa. Such modifications may be made in cells ex vivo.

In still other embodiments, the compositions and methods disclosed herein can be used to generate crop plants with improved traits or increased resistance to environmental stresses. The present disclosure can also be used to generate farm animal with improved traits or production animals. For example, pigs have many features that make them attractive as biomedical models, especially in regenerative medicine or xenotransplantation.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about" when used in relation to a numerical value, x, for example means x±5%.

As used herein, the terms "complementary" or "complementarity" refer to the association of double-stranded nucleic acids by base pairing through specific hydrogen bonds. The base paring may be standard Watson-Crick base pairing (e.g., 5'-A G T C-3' pairs with the complementary sequence 3'-T C A G-5'). The base pairing also may be Hoogsteen or reversed Hoogsteen hydrogen bonding. Complementarity is typically measured with respect to a duplex region and thus, excludes overhangs, for example. Complementarity between two strands of the duplex region may be partial and expressed as a percentage (e.g., 70%), if only some (e.g., 70%) of the bases are complementary. The bases that are not complementary are "mismatched." Complementarity may also be complete (i.e., 100%), if all the bases in the duplex region are complementary.

As used herein, the term "CRISPR/Cas system" refers to a complex comprising a CRISPR/Cas protein (i.e., nuclease, nickase, or catalytically dead protein) and a guide RNA.

The term "endogenous sequence," as used herein, refers to a chromosomal sequence that is native to the cell.

As used herein, the term "exogenous" refers to a sequence that is not native to the cell, or a chromosomal sequence whose native location in the genome of the cell is in a different chromosomal location.

A "gene," as used herein, refers to a DNA region (including exons and introns) encoding a gene product, as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "heterologous" refers to an entity that is not endogenous or native to the cell of interest. For example, a heterologous protein refers to a protein that is derived from or was originally derived from an exogenous source, such as an exogenously introduced nucleic acid sequence. In some instances, the heterologous protein is not normally produced by the cell of interest.

The terms "local chromatin structure" or "local chromatin configuration," as used herein, refers to nucleosomal structure and/or histone protein spacing, and generally does not refer to the compaction of nucleosomes into chromatin fibers and heterochromatin.

The term "nickase" refers to an enzyme that cleaves one strand of a double-stranded nucleic acid sequence (i.e., nicks a double-stranded sequence). For example, a nuclease with double strand cleavage activity can be modified by mutation and/or deletion to function as a nickase and cleave only one strand of a double-stranded sequence.

The term "nuclease," as used herein, refers to an enzyme that cleaves both strands of a double-stranded nucleic acid sequence.

The terms "nucleic acid" and "polynucleotide" refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogs of natural nucleotides, as well as nucleotides that are modified in the base, sugar and/or phosphate moieties (e.g., phosphorothioate backbones). In general, an analog of a particular nucleotide has the same base-pairing specificity; i.e., an analog of A will base-pair with T.

The term "nucleotide" refers to deoxyribonucleotides or ribonucleotides. The nucleotides may be standard nucleotides (i.e., adenosine, guanosine, cytidine, thymidine, and uridine), nucleotide isomers, or nucleotide analogs. A nucleotide analog refers to a nucleotide having a modified purine or pyrimidine base or a modified ribose moiety. A nucleotide analog may be a naturally occurring nucleotide (e.g., inosine, pseudouridine, etc.) or a non-naturally occurring nucleotide. Non-limiting examples of modifications on the sugar or base moieties of a nucleotide include the addition (or removal) of acetyl groups, amino groups, carboxyl groups, carboxymethyl groups, hydroxyl groups, methyl groups, phosphoryl groups, and thiol groups, as well as the substitution of the carbon and nitrogen atoms of the bases with other atoms (e.g., 7-deaza purines). Nucleotide analogs also include dideoxy nucleotides, 2'-O-methyl nucleotides, locked nucleic acids (LNA), peptide nucleic acids (PNA), and morpholinos.

The terms "polypeptide" and "protein" are used interchangeably to refer to a polymer of amino acid residues.

The term "proximal site," as used herein, refers to a binding site or nucleotide sequence that is located within about 250 base pairs on either side of a target sequence in chromosomal DNA.

As used herein, the term "programmable DNA modification protein" refers to a protein that is engineered to bind a specific target sequence in chromosomal DNA and which modifies the DNA or protein(s) associated with DNA at or near the target sequence.

The term "programmable DNA binding protein," as used herein, refers to a protein that is engineered to bind a specific target sequence in chromosomal DNA, but said protein does not modify the DNA or protein(s) associated with DNA at or near the target sequence.

The terms "target sequence," "target chromosomal sequence," and "target site" are used interchangeably to refer to the specific sequence in chromosomal DNA to which the programmable DNA modification protein is targeted, and the site at which the programmable DNA modification protein modifies the DNA or protein(s) associated with the DNA.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found on the GenBank website.

As various changes could be made in the above-described cells and methods without departing from the scope of the invention, it is intended that all matter contained in the above description and in the examples given below, shall be interpreted as illustrative and not in a limiting sense.

ENUMERATED EMBODIMENTS

The following enumerated embodiments are presented to illustrate certain aspects of the present invention, and are not intended to limit its scope.

1. A composition comprising: (a) a programmable DNA modification protein or nucleic acid encoding the programmable DNA modification protein; and (b) at least one programmable DNA binding protein or nucleic acid encoding the at least one programmable DNA binding protein.

2. The composition of embodiment 1, wherein the programmable DNA modification protein is a RNA-guided clustered regularly interspersed short palindromic repeats (CRISPR)/CRISPR-associated (Cas) (CRISPR/Cas) nuclease system, a CRISPR/Cas dual nickase system, a zinc finger nuclease (ZFN), a transcription activator-like effector nuclease (TALEN), a meganuclease, a fusion protein comprising a programmable DNA binding domain linked to a nuclease domain, or a fusion protein comprising a programmable DNA binding domain linked to a non-nuclease domain.

3. The composition of embodiment 2, wherein the programmable DNA binding domain of the fusion protein is a catalytically inactive CRISPR/Cas system, a catalytically inactive meganuclease, a zinc finger protein, or a transcription activator-like effector.

4. The composition of embodiment 2 or 3, wherein the non-nuclease domain of the fusion protein has acetyltransferase activity, deacetylase activity, methyltransferase activity, demethylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, citrullination activity, helicase activity, amination activity, deamination activity, alkylation activity, dealkylation activity, oxidation activity, transcriptional activation activity, or transcriptional repressor activity.

5. The composition of embodiment 4, wherein the non-nuclease domain of the fusion protein has cytosine deaminase activity, histone acetyltransferase activity, transcriptional activation activity, or transcriptional repressor activity.

6. The composition of any one of embodiments 1 to 5, wherein the at least one programmable DNA binding protein is a catalytically inactive CRISPR/Cas protein, a catalytically inactive meganuclease, a zinc finger protein, a transcription activator-like effector, a CRISPR/Cas nickase, a ZFN nickase, a TALEN nickase, or a meganuclease nickase.

7. The composition of any one of embodiments 1 to 6, wherein nucleic acid encoding the programmable DNA modification protein and the at least one programmable DNA binding protein is RNA or DNA, and/or wherein said nucleic acid is part of a plasmid vector or a viral vector.

8. The composition of any one of embodiments 1 to 6, wherein the programmable DNA modification protein is a CRISPR/Cas nuclease system, a CRISPR/Cas dual nickase system, or catalytically inactive CRISPR/Cas system linked to a non-nuclease domain, and the at least one programmable DNA binding protein is a catalytically inactive CRISPR/Cas system, wherein each CRISPR/Cas system comprises a CRISPR/Cas protein and a guide RNA.

9. The composition of embodiment 8, wherein each CRISPR/Cas nuclease system is a type I CRISPR/Cas system, a type II CRISPR/Cas system, a type III CRISPR/Cas system, or a type V CRISPR/Cas system.

10. The composition of embodiment 9, wherein each CRISPR/Cas nuclease system is a type II CRISPR/Cas system or a type V CRISPR/Cas system.

11. The composition of any one of embodiments 8 to 10, wherein nucleic acid encoding each CRISPR/Cas protein is mRNA or DNA.

12. The composition of any one of embodiments 8 to 11, wherein nucleic acid encoding each CRISPR/Cas protein and/or nucleic acid encoding each guide RNA is part of a plasmid vector or a viral vector.

13. The composition of any one of embodiments 8 to 11, wherein the guide RNA of each CRISPR/Cas system is enzymatically synthesized.

14. The composition of any one of embodiments 8 to 11, wherein the guide RNA of each CRISPR/Cas system is at least partially chemically synthesized.

15. A kit comprising the composition of any one of embodiments 1 to 14.

16. A method for increasing targeted genome modification efficiency and/or specificity in a eukaryotic cell, the method comprising introducing into the eukaryotic cell:

(a) a programmable DNA modification protein or nucleic acid encoding the programmable DNA modification protein and;

(b) at least one programmable DNA binding protein or nucleic acid encoding the at least one programmable DNA binding protein;

wherein the programmable DNA modification protein is targeted to a target chromosomal sequence and each of the at least one programmable DNA binding protein is targeted to a site proximal to the target chromosomal sequence, and binding of the at least one programmable DNA binding protein to the site proximal to the target chromosomal sequence increases accessibility of the programmable DNA modification protein to the target chromosomal sequence, thereby increasing targeted genome modification efficiency and/or specificity.

17. The method of embodiment 16, wherein the site proximal to the target chromosomal sequence is located within about 250 base pairs on either side of the target chromosomal sequence.

18. The method of embodiment 17, wherein the wherein the site proximal to the target chromosomal sequence is located within about 100 base pairs on either side of the target chromosomal sequence.

19. The method of embodiment 18, wherein the wherein the site proximal to the target chromosomal sequence is located within about 75 base pairs on either side of the target chromosomal sequence.

20. The method of embodiment 19, wherein the wherein the site proximal to the target chromosomal sequence is located within about 50 base pairs on either side of the target chromosomal sequence.

21. The method of embodiment 20, wherein the wherein the site proximal to the target chromosomal sequence is located within about 25 base pairs on either side of the target chromosomal sequence.

22. The method of any one of embodiments 16 to 21, wherein the programmable DNA modification protein is CRISPR/Cas nuclease system, a CRISPR/Cas dual nickase system, a zinc finger nuclease (ZFN), a transcription activator-like effector nuclease (TALEN), a meganuclease, a fusion protein comprising a programmable DNA binding domain linked to a nuclease domain, or a fusion protein comprising a programmable DNA binding domain linked to a non-nuclease domain.

23. The method of embodiment 22, wherein the programmable DNA binding domain of the fusion protein is a catalytically inactive CRISPR/Cas system, a catalytically inactive meganuclease, a zinc finger protein, or a transcription activator-like effector.

24. The method of embodiment 22 or 23, wherein the non-nuclease modification domain of the fusion protein has acetyltransferase activity, deacetylase activity, methyltransferase activity, demethylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, demyristoylation activity, citrullination activity, helicase activity, amination activity, deamination activity, alkylation activity, dealkylation activity, oxidation activity, transcriptional activation activity, or transcriptional repressor activity.

25. The method of embodiment 24, wherein the non-nuclease domain of the fusion protein has cytosine deaminase activity, histone acetyltransferase activity, transcriptional activation activity, or transcriptional repressor activity.

26. The method of any one of embodiments 16 to 25, wherein the at least one programmable DNA binding protein is a catalytically inactive CRISPR/Cas system, a catalytically inactive meganuclease, a zinc finger protein, a transcription activator-like effector, a CRISPR/Cas nickase, a ZFN nickase, a TALEN nickase, or a meganuclease nickase.

27. The method of any one of embodiments 16 to 26, wherein the programmable DNA modification protein is a CRISPR/Cas nuclease system, a CRISPR/Cas dual nickase system, or catalytically inactive CRISPR/Cas system linked to a non-nuclease domain, and the at least one programmable DNA binding protein is a catalytically inactive CRISPR/Cas system, wherein each CRISPR/Cas system comprises a CRISPR/Cas protein and a guide RNA.

28. The method of embodiment 27, wherein the guide RNA of each CRISPR/Cas system is at least partially chemically synthesized.

29. The method of embodiment 27, wherein the guide RNA of each CRISPR/Cas system is enzymatically synthesized.

30. The method of any one of embodiments 16 to 29, wherein the eukaryotic cell is in vitro.

31. The method of any one of embodiments 16 to 29, wherein the eukaryotic cell is in vivo.

32. The method of any one of embodiments 16 to 31, wherein the eukaryotic cell is a mammalian cell.

33. The method of embodiment 32, wherein the mammalian cell is a human cell.

34. The method of embodiment 32, wherein the mammalian cell is a non-human cell.

35. A method for detecting a chromosomal sequence in a eukaryotic cell, the method comprising:

I. introducing into the eukaryotic cell (a) a programmable DNA binding protein comprising at least one detectable marker domain or nucleic acid encoding the programmable DNA binding protein comprising at least one detectable marker domain; and (b) at least one programmable DNA binding protein or nucleic acid encoding the at least one programmable DNA binding protein, wherein the programmable DNA binding protein comprising at least one detectable marker domain is targeted to a target chromosomal sequence and each of the at least one programmable DNA binding protein is targeted to a site proximal to the target chromosomal sequence, and binding of the at least one programmable DNA binding protein to the site proximal to the target chromosomal sequence increases accessibility of the programmable DNA binding protein comprising at least one detectable marker domain to the target chromosomal sequence; and II. detecting the programmable DNA binding protein comprising at least one detectable marker domain bound to the target chromosomal sequence.

36. The method of embodiment 35, wherein the site proximal to the target chromosomal sequence is located within about 250 base pairs on either side of the target chromosomal sequence.

37. The method of embodiment 36, wherein the wherein the site proximal to the target chromosomal sequence is located within about 100 base pairs on either side of the target chromosomal sequence.

38. The method of embodiment 37, wherein the wherein the site proximal to the target chromosomal sequence is located within about 75 base pairs on either side of the target chromosomal sequence.

39. The method of embodiment 38, wherein the wherein the site proximal to the target chromosomal sequence is located within about 50 base pairs on either side of the target chromosomal sequence.

40. The method of embodiment 39, wherein the wherein the site proximal to the target chromosomal sequence is located within about 25 base pairs on either side of the target chromosomal sequence.

41. The method of any one of embodiments 35 to 40, wherein the at least one detectable marker domain of the programmable DNA binding protein comprising at least one detectable marker domain is a fluorescent protein, a fluorescent tag, an epitope tag, or a naturally occurring epitope within the programmable DNA binding protein.

42. The method of any one of embodiments 35 to 41, wherein the programmable DNA binding protein comprising at least one detectable marker domain is a catalytically inactive CRISPR/Cas system linked to at least one detectable marker domain, a catalytically inactive meganuclease linked to at least one detectable marker domain, a zinc finger protein linked to at least one detectable marker domain, or a transcription activator-like effector linked to at least one detectable marker domain.

43. The method of any one of embodiments 35 to 42, wherein the at least one programmable DNA binding protein is a catalytically inactive CRISPR/Cas system, a catalytically inactive meganuclease, a zinc finger protein, a transcription activator-like effector, a CRISPR/Cas nickase, a ZFN nickase, a TALEN nickase, or a meganuclease nickase.

44. The method of any one of embodiments 35 to 43, wherein the programmable DNA binding protein comprising at least one detectable marker domain is a catalytically inactive CRISPR/Cas system linked to at least one detectable marker domain, and the at least one programmable DNA binding protein is a catalytically inactive CRISPR/Cas system, wherein each CRISPR/Cas system comprises a CRISPR/Cas protein and a guide RNA.

45. The method of embodiment 44, where the guide RNA of each CRISPR/Cas system is at least partially chemically synthesized.

46. The method of embodiment 44, where the guide RNA of each CRISPR/Cas system is enzymatically synthesized.

47. The method of any one of embodiments 35 to 46, wherein the eukaryotic cell is a mammalian cell.

48. The method of embodiment 47, wherein the mammalian cell is a human cell.

49. The method of embodiment 47, wherein the mammalian cell is a non-human cell.

50. The method of any one of embodiments 35 to 49, wherein the eukaryotic cell is live or fixed.

51. The method of any one of embodiments 35 to 50, wherein the detecting comprises dynamic live cell imaging, fluorescent microscopy, confocal microscopy, immunofluorescence, immunodetection, RNA-protein binding, or protein-protein binding.

EXAMPLES

The following examples illustrate certain aspects of the disclosure.

Example 1. *Francisella novicida* CRISPR-Cas9 (FnCas9) Gene Editing Enhancement

FnCas9 is a type IIB CRISPR-Cas9. It exhibits a higher intrinsic specificity than the widely used SpCas9, but is has been found to be less robust than SpCas9 in human cells. To determine whether the binding of programmable DNA binding proteins to proximal sites could enable the nuclease to cleave an otherwise inaccessible target (i.e., POR locus) in human cells, K562 cells were transfected with 5.6 µg of FnCas9 plasmid DNA, 5 µg of catalytically dead SpCas9 (SpdCas9) plasmid DNA, and 3 µg of plasmid DNA of each sgRNA per one million of cells (see FIG. 2). Genomic DNA was harvested 3 days after transfection and the target region was amplified by PCR with the forward primer 5'-CTCCCTGCTTCTTGTCGTAT-3' (SEQ ID NO:9) and the reverse primer 5'-ACAGGTCGTGGACACTCACA-3' (SEQ ID NO:10). Targeted insertions/deletions (indels) by FnCas9 on the target were determined by Cel-I nuclease digestion and polyacrylamide gel analysis.

Figure 2:
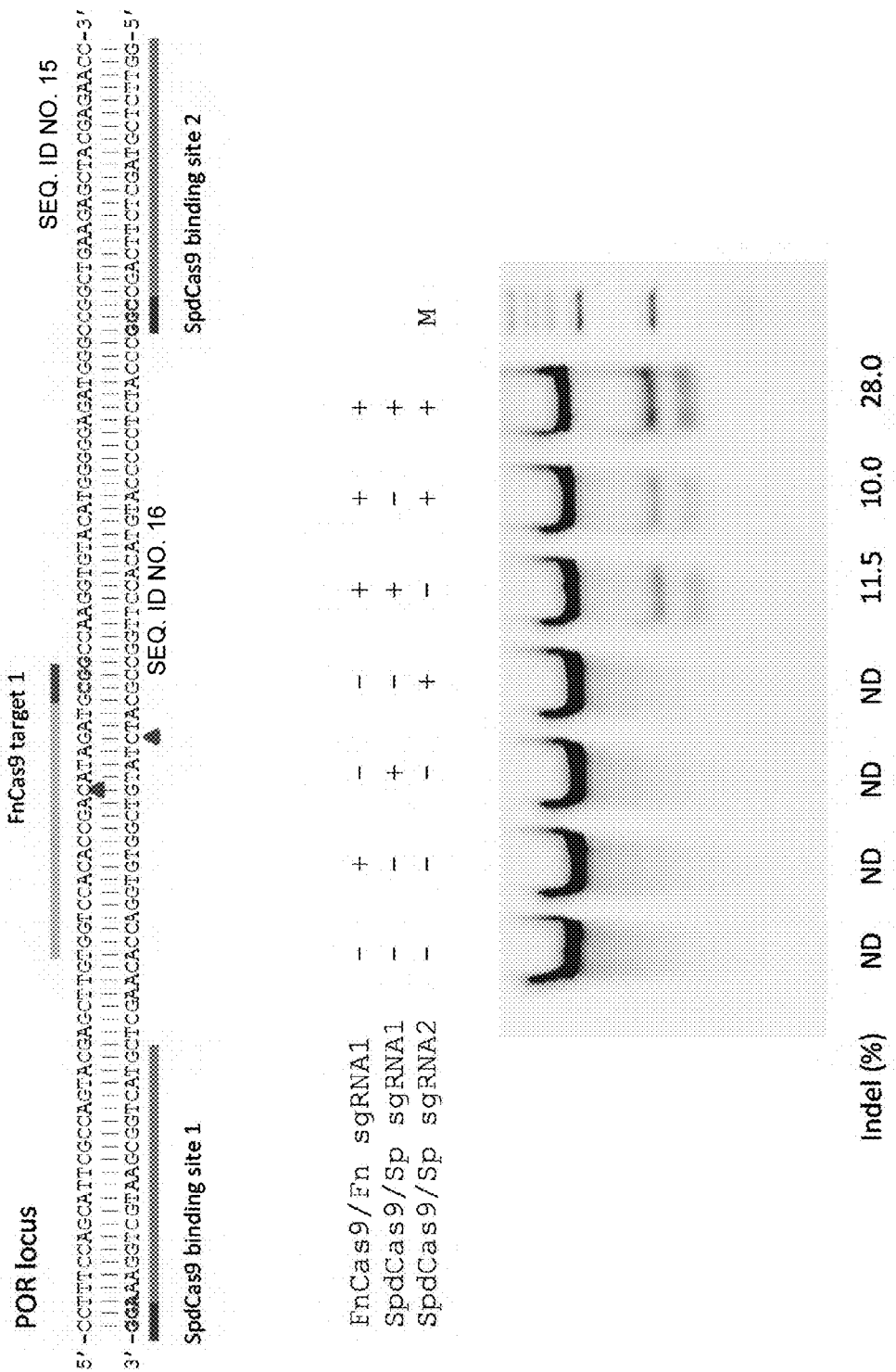
FIG. 2 illustrates that the binding of catalytically inactive SpCas9 (SpdCas9) to proximal site(s) increases the efficiency of cleavage by FnCas9. The sequences presented at the top show the relative locations of the FnCas9 target site in the POR locus and the binding sites of SpdCas9. The results of a Cel-I nuclease assay are shown at the bottom.

As shown in FIG. 2, FnCas9 was unable to cleave the target when transfected alone. But, when it was transfected in combination with SpdCas9 to help disrupt the local chromatin configuration, FnCas9 was able to cleave the target at robust levels, with 10-11% of indels, when SpdCas9 was used to bind one proximal site. When SpdCas9 was used to bind two proximal sites, FnCas9 activity further increased to 28% of indels. These results demonstrate that the method disclosed herein can enable an endonuclease to cleave an otherwise inaccessible target efficiently, and there is a synergistic effect between two sites used to disrupting the local chromatin configuration.

Example 2. *Campylobacter jejuni* CRISPR-Cas9 (CjCas9) Gene Editing Enhancement

Figure 3A:
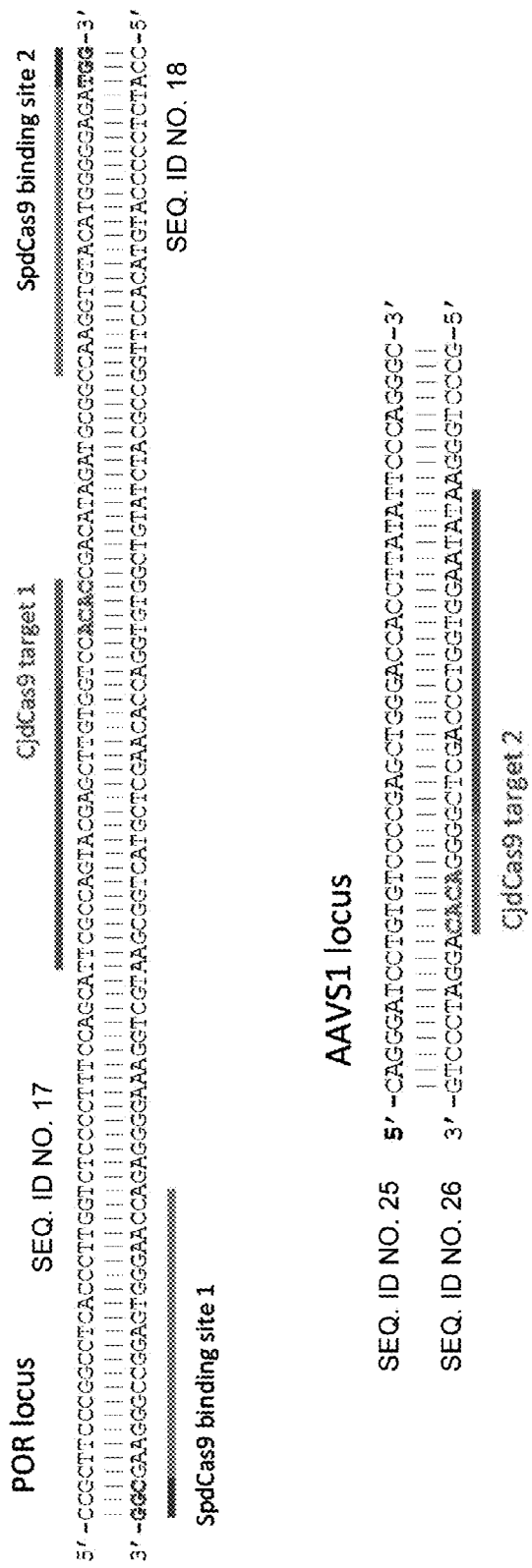
FIG. 3A illustrates the design of an experiment to determine whether binding of catalytically inactive SpCas9 (SpdCas9) increases the accessibility and binding of epitope-tagged FLAG®-tagged) catalytically inactive CjCas9 (CjdCas9) to a previously inaccessible site in the POR locus.
Figure 3B:
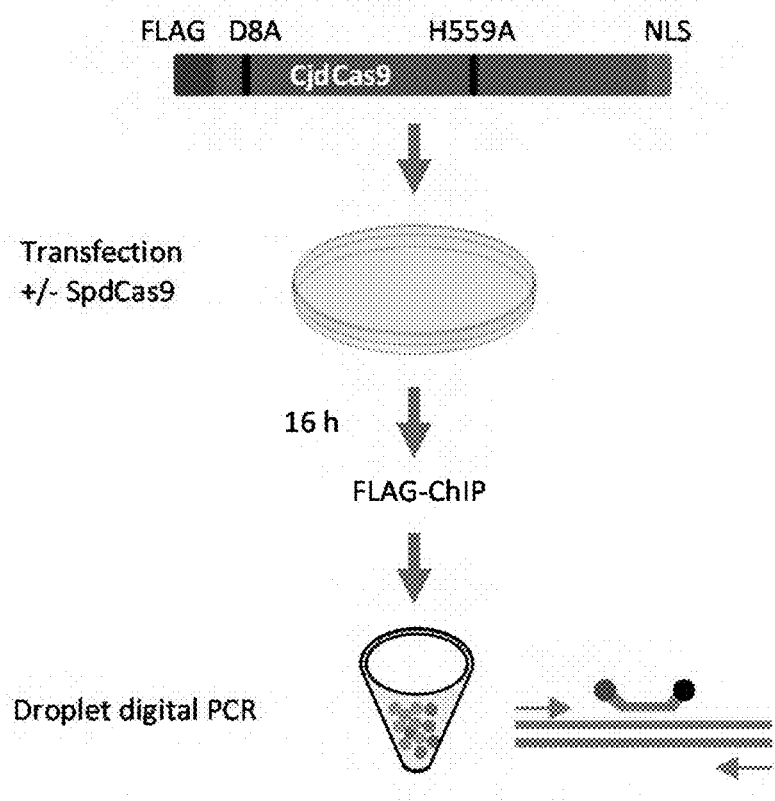
FIG. 3B provides a diagram of the chromatin immunoprecipitation binding assay used to detect binding of epitope-tagged CjdCas9 to target sites in the POR and AAVS1 loci.

CjCas9 is a type IIC CRISPR-Cas9. It is the smallest Cas9 characterized thus far and has a unique ACAY PAM requirement. But the nuclease has been found to be inactive on most targets in human cells. To determine whether the methods disclosed herein could enable the CjCas9 protein to bind an inaccessible target in human cells, K562 cells were transfected with 4.2 µg of Flag-tagged catalytically dead CjCas9 (CjdCas9) plasmid DNA, 5 µg of catalytically dead SpCas9 (SpdCas9) plasmid DNA, and 3 µg of plasmid DNA of each sgRNA per one million of cells (see FIG. 3A). Cells were fixed in formaldehyde 16 hours after transfection and chromatin immunoprecipitation (ChIP) was carried out using anti-flag antibody. Target binding by Flag-CjdCas9 was determined by droplet digital PCR (ddPCR).

Figure 3C:
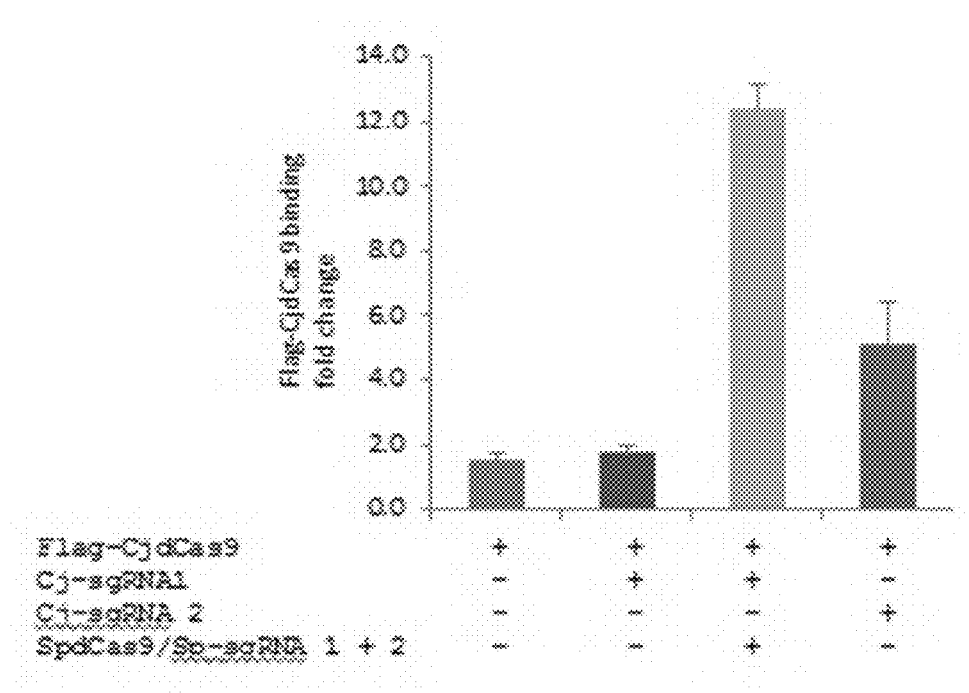
FIG. 3C illustrates that the binding of SpdCas9 to proximal sites increases the binding of epitope-tagged CjCas9 to a previously inaccessible site in the POR locus.

As shown in FIG. 3C, Flag-CjdCas9 was able to bind a previously known accessible target in the AAVS1 locus, but was unable to bind an inaccessible target in the POR locus when it was transfected alone. However, when it was transfected in combination with SpdCas9 to disrupt local chromatin configuration, Flag-CjdCas9 was able to bind the POR target even more efficiently than its binding of the AAVS1 target.

Figure 4:
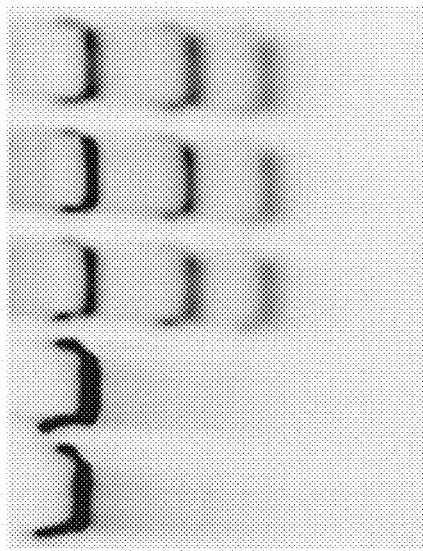
FIG. 4 illustrates that the binding of catalytically inactive SpCas9 (SpdCas9) to proximal site(s) increases the efficiency of cleavage by CjCas9. The sequences presented at the top show the relative locations of the CjCas9 target site in the POR locus and the binding sites of SpdCas9. The results of a Cel-I nuclease assay are shown at the bottom.

To examine the effect on target DNA cleavage, K562 cells were transfected with 4.2 µg of CjCas9 plasmid DNA, 5 µg of SpdCas9 plasmid DNA, and 3 µg of plasmid DNA of each sgRNA per one million of cells. Genomic DNA was harvested 3 days after transfection and the target region was amplified by PCR with the forward primer 5'-CTCCCCT-GCTTCTTGTCGTAT-3' (SEQ ID NO:9) and the reverse primer 5'-ACAGGTCGTGGACACTCACA-3' (SEQ ID NO:10). CjCas9 cleavage activity on the POR target was determined by Cel-I nuclease digestion and polyacrylamide gel analysis. As shown in FIG. 4, CjCas9 was unable to cleave the target without SpdCas9. But, when it was transfected in combination with SpdCas9, CjCas9 was able to cleave the target efficiently with 34.1-37.9% of indels. These results demonstrate that the method disclosed herein can enable a nuclease to bind and cleave an otherwise inaccessible target efficiently.

Example 3. *Francisella novicida* Cpf1 (FnCpf1) Gene Editing Enhancement

FnCpf1 is a type V CRISPR-Cas system. Cpf1 systems are significantly divergent from type II CRISPR-Cas9 systems. Unlike Cas9 systems, Cpf1 systems use a 5' T rich PAM and a single RNA guide for targeting without a tracrRNA (Zetsche et al., Cell, 2015, 163:1-13). These "newer" CRISPR systems have potential to make the gene editing practice even simpler, but many Cpf1 systems have been found to be inactive in human cells. To determine whether the methods disclosed herein could enable the divergent, "inactive" Cpf1 nuclease to cleave endogenous targets in human cells, K562 cells were transfected with 5 µg of FnCpf1 plasmid DNA, 5 µg of SpdCas9 plasmid DNA, and 3 µg of plasmid DNA of each sgRNA per one million of cells (see FIG. 5). Genomic DNA was harvested 3 days after transfection and the target region was amplified by PCR with the forward primer 5'-CTCCCCTGCTTCTTGTCGTAT-3' (SEQ ID NO:9) and the reverse primer 5'-ACAGGTCGTG-GACACTCACA-3' (SEQ ID NO:10). FnCpf1 cleavage activity on a POR target was determined by Cel-I nuclease digestion and polyacrylamide gel analysis.

Figure 5:
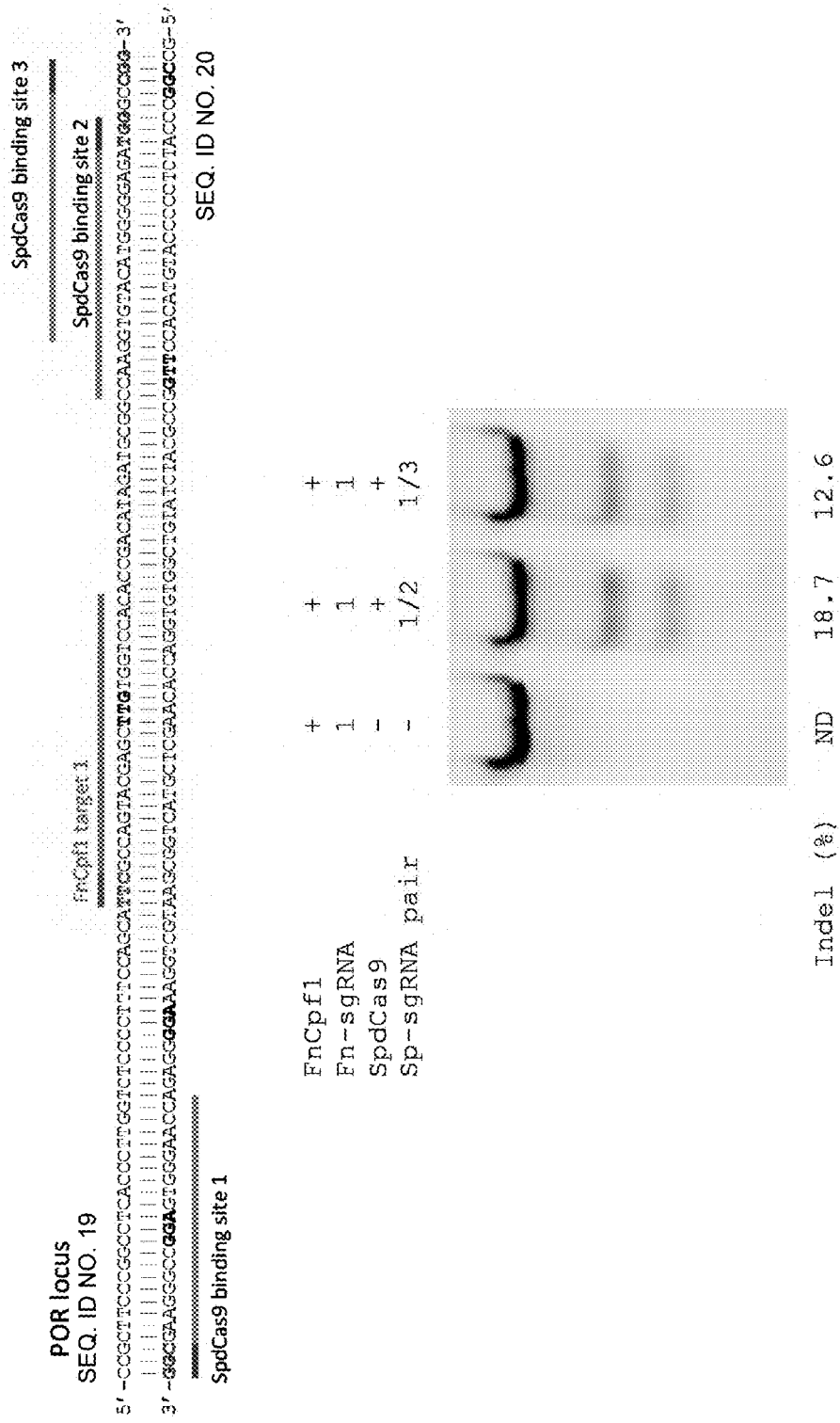
FIG. 5 illustrates that the binding of catalytically inactive SpCas9 (SpdCas9) to proximal site(s) increases the efficiency of cleavage by FnCpf1. The relative locations of the FnCpf1 target site and SpdCas9 binding sites in the POR locus are illustrated at the top and the results of a Cel-I nuclease assay are shown at the bottom.

As shown in FIG. 5, FnCpf1 was unable to cleave the target when it was transfected alone, but was able to cleave the target efficiently when it was transfected in combination of SpdCas9. These results demonstrate that the method disclosed herein is applicable to divergent type V CRISPR-Cas systems.

Example 4. Selective Editing Between Identical Targets in Human HBB and HBD

Two identical targets in human (i.e., HBB and HBD) were used to determine whether the methods disclosed herein could facilitate selective editing between identical sites in different genes. K562 cells were transfected with 4.2 µg of CjCas9 plasmid DNA, 5 µg of SpdCas9 plasmid DNA, and 3 µg of plasmid DNA of each sgRNA per one million of cells (see FIG. 6). Genomic DNA was harvested 3 days after transfection and the two target regions were amplified by PCR with the forward primer 5'-CGGCTGTCATCACTTA-GACCTCA-3' (SEQ ID NO:11) and the reverse primer 5'-GCAGCCTAAGGGTGGGAAAATAGA-3' (SEQ ID NO:12) for HBB, and the forward primer 5'-AGGGCAAGTTAAGGGAATAGTGGAA-3' (SEQ ID NO:13) and the reverse primer 5'-CCAAGGGTAGACCAC-CAGTAATCTG-3' (SEQ ID NO:14) for HBD. CjCas9 cleavage activity on the HBB and HBD targets were determined by Cel-I nuclease digestion and polyacrylamide gel analysis.

Figure 6:
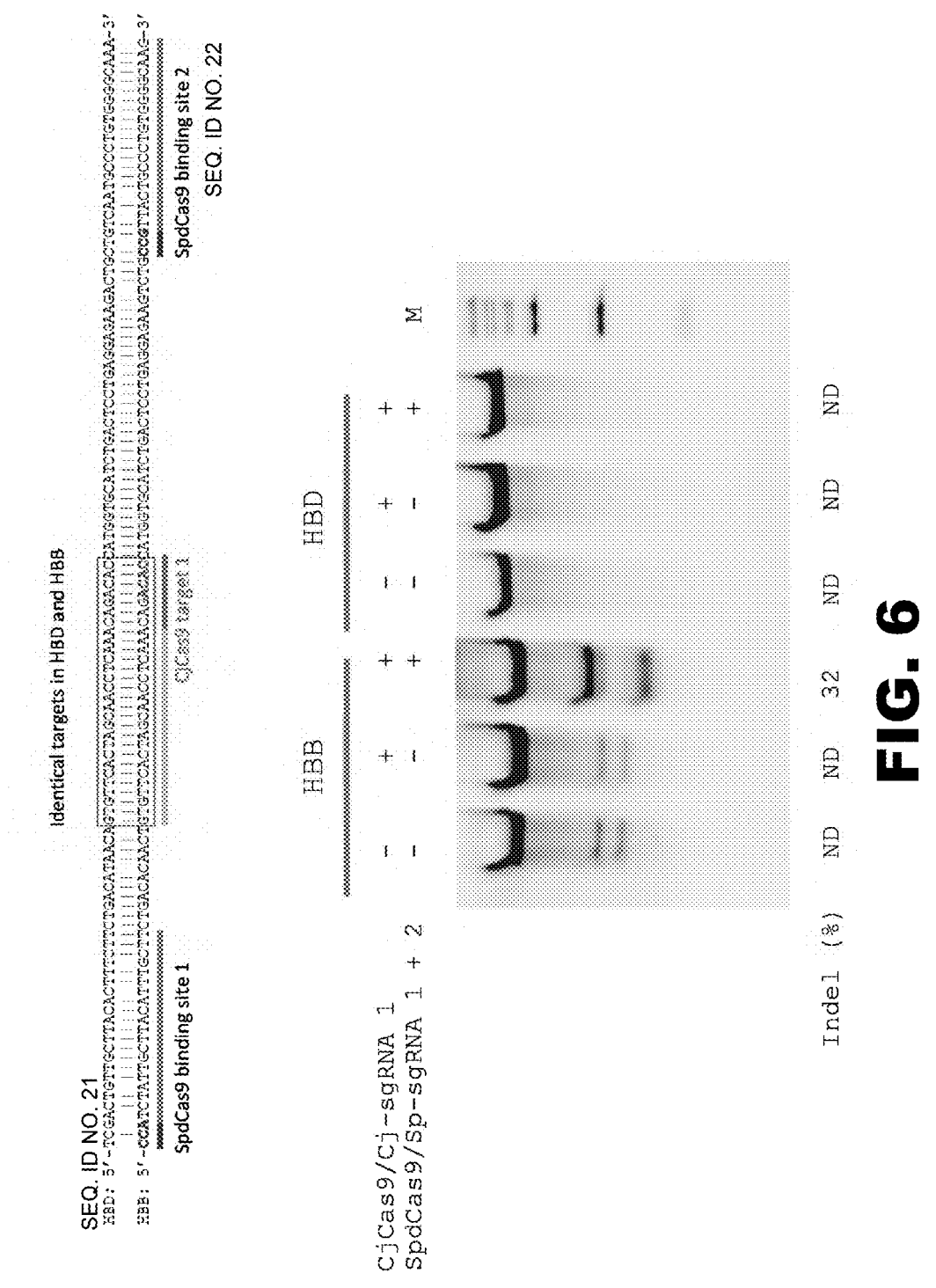

As shown in FIG. 6, when it was transfected alone, CjCas9 was unable to cleave either target. But, when it was transfected in combination with SpdCas9 targeted to sites proximal to HBB, CjCas9 cleaved the HBB target efficiently but was still unable to cleave the identical HBD target. The two Cel-I nuclease digestion bands in the first two lanes were caused by SNPs present in the K562 cell population. These results demonstrate the unique capability of the disclosed method to improve gene editing selectivity.

Example 5. *Streptococcus pyogenes* CRISPR-Cas9 (SpCas9) Gene Editing Enhancement SpCas9 is a type IIA CRISPR-Cas9, and has been widely used in genome modification because of its robust activity in eukaryotic cells. However, its activity can also vary widely from target to target. To determine whether the methods disclosed herein could also enhance this nuclease, K562 cells were transfected with 5 µg of SpCas9 plasmid DNA, 5.6 µg of catalytically dead FnCas9 (FndCas9), and 3 µg of plasmid DNA of each sgRNA per one million of cells (see FIG. 7). Genomic DNA was harvested 3 days after transfection and the target region was amplified by PCR with the forward primer 5'-CTCCCCTGCTTCTTGTCGTAT-3' (SEQ ID NO:9) and the reverse primer 5'-ACAGGTCGTG-GACACTCACA-3' (SEQ ID NO:10). SpCas9 cleavage activity on the POR target was determined by Cel-I nuclease digestion and polyacrylamide gel analysis.

Figure 7:
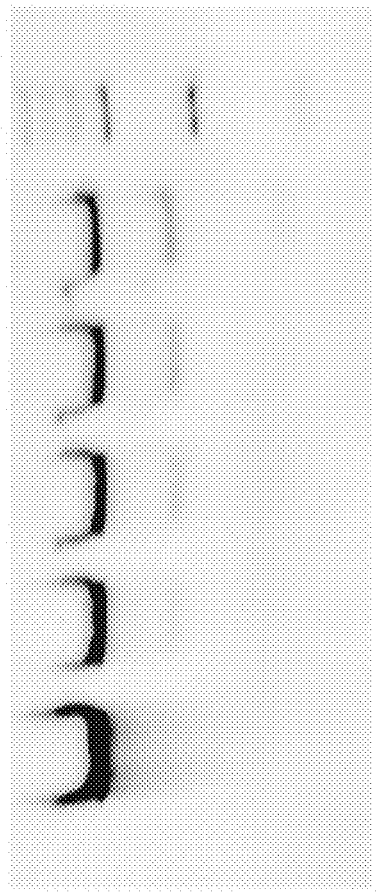
FIG. 7 illustrates that the binding of catalytically inactive FnCas9 (FndCas9) to proximal site(s) increases the specific cleavage by SpCas9. The relative locations of the SpCas9 target site and the FndCas9 binding sites in the POR locus are indicated at the top. The results of a Cel-I nuclease assay are shown at the bottom.

As shown in FIG. 7, SpCas9 cleavage activity increased significantly when it was transfected in combination with FndCas9, compared to when it was transfected alone. These results show that the method disclosed herein can also be applied to robust endonucleases.

Example 6. Enhancement of Gene Editing Using ssDNA Oligo Donor

Figure 8:
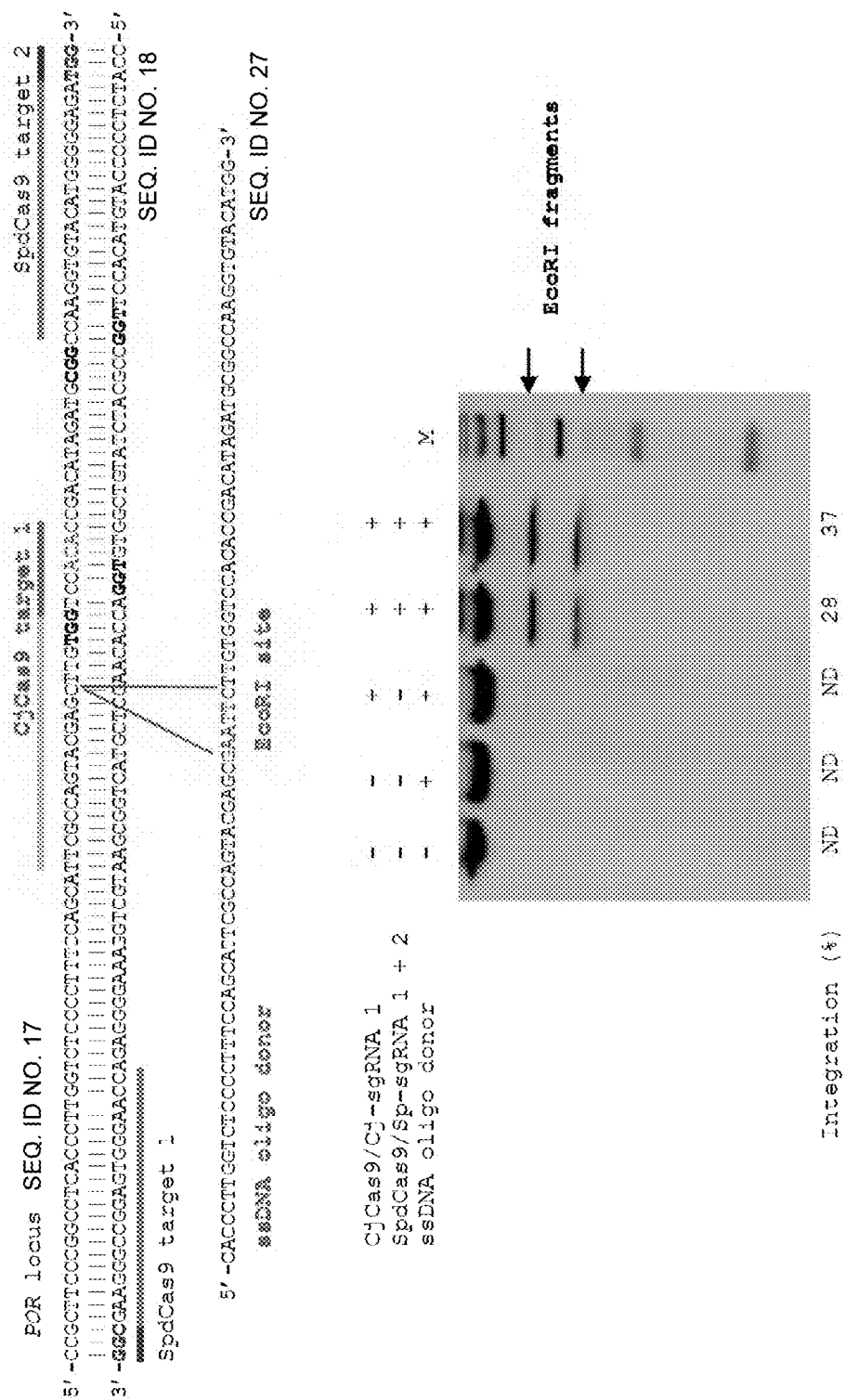
FIG. 8 illustrates the enhancement of ssDNA oligo-mediated gene editing. The relative locations of the target sites in the POR locus and the sequence of the ssDNA oligo are shown at the top. The results of the EcoRI site targeted integration are shown at the bottom. EcoRI site integration efficiencies (%) were determined by ImageJ. M: Wide-range DNA markers. ND: not determined.

K562 cells were transfected with 4.2 µg of CjCas9 plasmid DNA, 5 µg of SpdCas9 plasmid DNA, 3 µg of plasmid DNA of each sgRNA, and 300 pmol of an 88-nt ssDNA oligo donor for targeted integration of an EcoRI restriction site, per one million of cells. Genomic DNA was harvested 3 days after transfection and the target region was amplified by PCR with the forward primer 5'-CTCCCCTGCTTCTT-GTCGTAT-3' (SEQ ID NO:9) and the reverse primer 5'-ACAGGTCGTGGACACTCACA-3' (SEQ ID NO:10). Targeted integration of the EcoRI restriction site was determined by digestion with EcoRI restriction enzyme and polyacrylamide gel analysis. As shown in FIG. 8, the restriction site was integrated efficiently (28-37%) in the POR locus when the ssDNA oligo donor was transfected in concert with CjCas9 and SpdCas9, while no integration was detected when the oligo donor was either transfected alone or in combination with CjCas9 without SpdCas9. These results demonstrate that the method disclosed herein can facilitate efficient gene editing using ssDNA oligo donor on an otherwise inaccessible target.

Example 7. Enhancement of Sequence Specific Genomic DNA Detection in Live and Fixed Cells Fusion of Cas9 proteins to fluorescent proteins has enabled detection of chromosomal dynamics in live cells (Chen et al., Cell, 2013, 155:1479-91). It is therefore believed that chromatin structural dynamics will influence the ability of CRISPR/Cas system complexes to access various genomic loci. Thus, the placement of CRISPR (dCas9) complexes proximal those harboring dCas9-GFP is believed to enhance the detection of chromosomal dynamics to an extent similar to that observed in Example 2 for chromatin immunoprecipitation. For example, CjdCas9 can be fused to GFP and targeted to a region with a chromatin state that prevents detectable binding of CjdCas9-GFP. SpdCas9-based system can then be designed in proximity to CjdCas9-GFP targets to produce detectable signal. For chromatin regions that are resistant to binding and detection of SpdCas9-GFP, a proximal FndCas9 molecule may be used to enhance detection to an extent similar to that shown in Example 5 for SpCas9 and FndCas9 proximal targeting and enhancement of double strand break activity. Furthermore, given that previous studies have indicated that the extent of hybridization requirements between CRISPR guide RNA and genomic DNA maybe less for binding than for double strand cleavage (Wu et al., Nature Biotechnology, 2014, 32(7): 670-6), the use of proximal CRISPR binding is believed to increase signal-to-noise ratios for detection of genomic DNA in cells.

Similar CRISPR-based detection methods have been applied to fixed cells (Deng et al., Proc. Natl. Acad, Sci. USA, 2015, 112(38):11870-75). Thus, it is believed that proximal CRISPR targeting will enhance detection of fixed DNA in a manner similar to that described above for live cells. Since genomic DNA strands in fixed cells are chemically cross-linked, interrogation of sequence information by hybridization of nucleic acid probes typically requires a pre-treatment step with heat or chemical processing to separate strands sufficiently. It is therefore possible that proximal CRISPR targeting will render fixed DNA more accessible and reduce the extent (or requirement) for heat or chemical treatment of fixed cells. Elimination of heat or chemical treatment would provide advantages in diagnostic protocol simplification and maintenance of intracellular molecular structures that better reflect live cell biology and therefore more informed diagnostic outcomes.

Example 8. Enhancement of CRISPR-Based Gene Activation and Repression in Eukaryotic Cells Fusion of Cas9 proteins to transcriptional regulation domains has enabled targeted gene activation and repression (Konermann et al., Nature, 2014; 517(7536):583-8; Gilbert et al., Cell, 2014, 159(3):547-661). It is believed that chromatin structural dynamics will influence the ability of the CRISPR complex to access various genomic loci and induce activation or repression. Thus, the placement of CRISPR (dCas9) complexes proximal those harboring dCas9 fused to transcription regulation domains is believed to enhance the targeted gene regulation to an extent similar to that observed in Example 2 for chromatin immunoprecipitation. For chromatin regions that are resistant to binding and modification by SpdCas9-transcriptional-regulators, a proximal FndCas9 molecule can be used to enhance gene activation or repression to an extent similar to that shown in Example 5 for SpCas9 and FndCas9 proximal targeting and enhancement of double strand break activity.

Example 9. Enhancement of CRISPR-Based Epigenetic Modification in Eukaryotic Cells Fusion of Cas9 proteins to epigenetic modification domains has enabled targeted epigenetic chromosomal modifications such as histone acetylation by p300 or cytosine deamination by cytosine deaminase (Hilton et al., Nat. Biotechnol; 2015, 33(5):510-7; Komor et al., Nature, 2016, 533(7603):420-4). It is believed that chromatin structural dynamics will influence the ability of the CRISPR complex to access various genomic loci. Thus, the placement of CRISPR (dCas9) complexes proximal those harboring dCas9 fused to epigenetic modifiers should enhance the targeted epigenetic modification of chromosomal DNA, local proteins, or local RNA to an extent similar to that observed in Example 2 for chromatin immunoprecipitation. For chromatin regions that are resistant to binding and modification by SpdCas9-epi-modifiers, a proximal FndCas9 molecule can be used to enhance detection to an extent similar to that shown in Example 5 for SpCas9 and FndCas9 proximal targeting and enhancement of double strand break activity.

What is claimed is:

1. A method for increasing targeted double-stranded cleavage activity and/or specificity at a target chromosomal region in a eukaryotic cell, the method comprising introducing into the eukaryotic cell:
   (a) a CRISPR system having binding activity and double-stranded cleavage activity, or a nucleic acid encoding said CRISPR system, comprising (i) a catalytically active Type II CRISPR/Cas9 protein or a catalytically active Type V CRISPR/Cpf1 protein, and (ii) a guide RNA; and
   (b) at least one CRISPR system having binding activity but lacking cleavage activity, or a nucleic acid encoding said CRISPR system, comprising (i) a catalytically inactive Type II CRISPR/Cas9 protein or a catalytically inactive Type V CRISPR/Cpf1 protein, and (ii) a guide RNA;
   wherein the CRISPR system of subpart (a) and the at least one CRISPR system of subpart (b) are introduced into the eukaryotic cell in the absence of a donor polynucleotide;
   wherein the CRISPR system of subpart (a) is targeted to a target chromosomal sequence within the target chromosomal region and the at least one CRISPR system of subpart (b) is targeted to and, excluding any off-target chromosomal binding, binds solely to a site that is proximal to the target chromosomal sequence within the target chromosomal region, such that the CRISPR systems of subparts (a) and (b) are located in spatial proximity only by the chromosomal DNA binding action of their respective guide RNA and are within about 250 base pairs of one another on the target chromosomal region, and
   wherein binding of the at least one CRISPR system of subpart (b) to the site proximal to the target chromosomal sequence increases accessibility of the CRISPR system of subpart (a) to the target chromosomal sequence, thereby increasing targeted double-stranded cleavage activity and/or specificity.

2. The method of claim 1, wherein the CRISPR system of subpart (a) and the at least one CRISPR system of subpart (b) are within about 200 base pairs of one another on the target chromosomal region.

3. The method of claim 2, wherein the CRISPR system of subpart (a) and the at least one CRISPR system of subpart (b) are within about 100 base pairs of one another on the target chromosomal region.

4. The method of claim 3, wherein the CRISPR system of subpart (a) and the at least one CRISPR system of subpart (b) are within about 75 base pairs of one another on the target chromosomal region.

5. The method of claim 4, wherein the CRISPR system of subpart (a) and the at least one CRISPR system of subpart (b) are within about 50 base pairs of one another on the target chromosomal region.

6. The method of claim 5, wherein the CRISPR system of subpart (a) and the at least one CRISPR system of subpart (b) are within about 25 base pairs of one another on the target chromosomal region.

7. The method of claim 1, wherein the eukaryotic cell is in vitro.

8. The method of claim 1, wherein the eukaryotic cell is in vivo.

9. The method of claim 1, wherein the eukaryotic cell is a mammalian cell.

10. The method of claim 9, wherein the mammalian cell is a human cell.

11. The method of claim 1, wherein nucleic acid encoding each CRISPR system of subpart (a) and subpart (b) is mRNA or DNA.

12. The method of claim 1, wherein nucleic acid encoding each CRISPR system of subpart (a) and subpart (b) and/or encoding each guide RNA of subpart (a) and subpart (b) is part of a plasm id vector or a viral vector.

13. The method of claim 1, wherein the guide RNA of each CRISPR system of subpart (a) and subpart (b) is at least partially chemically synthesized.

14. The method of claim 1, wherein the guide RNA of each CRISPR system of subpart (a) and subpart (b) is enzymatically synthesized.

15. The method of claim 1, wherein the CRISPR system of subpart (a) comprises a catalytically active Type V CRISPR/Cpf1 protein and the at least one CRISPR system of subpart (b) comprises a catalytically inactive Type II CRISPR/Cas9 protein.

16. The method of claim 1, wherein the CRISPR system of subpart (a) comprises a catalytically active Type II CRISPR/Cas9 protein and the at least one CRISPR system of subpart (b) comprises a catalytically inactive Type II CRISPR/Cas9 protein.

17. The method of claim 1, wherein two CRISPR systems having binding activity but lacking cleavage activity are introduced into the eukaryotic cell.

18. The method of claim 1, wherein
   (i) the CRISPR system of subpart (a) is a Type IIB *Francisella novicida* CRISPR/Cas9 protein and the at least one CRISPR system of subpart (b) is a Type IIA *Streptococcus pyogenes* CRISPR/Cas9 protein;
   (ii) the CRISPR system of subpart (a) is a Type IIA *S. pyogenes* CRISPR/Cas9 protein and the at least one CRISPR system of subpart (b) is a Type IIB *F. novicida* CRISPR/Cas9 protein;

(iii) the CRISPR system of subpart (a) is a Type IIC *Campylobacter jejuni* CRISPR/Cas9 protein and the at least one CRISPR system of subpart (b) is a Type IIA *S. pyogenes* CRISPR/Cas9 protein; or
(iv) the CRISPR system of subpart (a) is a Type V *F. novicida* CRISPR/Cpf1 protein and the at least one CRISPR system of subpart (b) is a Type IIA *S. pyogenes* CRISPR/Cas9 protein.

* * * * *

UNITED STATES PATENT AND TRADEMARK OFFICE
CERTIFICATE OF CORRECTION

PATENT NO. : 10,266,851 B2
APPLICATION NO. : 15/437148
DATED : April 23, 2019
INVENTOR(S) : Fuqiang Chen Page 1 of 1

It is certified that error appears in the above-identified patent and that said Letters Patent is hereby corrected as shown below:

In the Claims

In Column [56], Line [39], in Claim [12] delete "plasm id" and insert -- plasmid --

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*